United States Patent [19]

Varma et al.

[11] Patent Number: 5,049,577

[45] Date of Patent: Sep. 17, 1991

[54] 2-PYRROLIDONE SUBSTITUTED DIHYDROXY ALKANOIC, ALKENOIC AND ALKYNOIC ACIDS, COMPOSITIONS AND HMG-COA REDUCTASE INHIBITION THEREWITH

[75] Inventors: Ravi K. Varma, Belle Mead; Eric M. Gordon, Pennington; Sam T. Chao, East Windsor, all of N.J.

[73] Assignee: E. R. Squibb & Sons, Inc., Princeton, N.J.

[21] Appl. No.: 471,461

[22] Filed: Jan. 29, 1990

[51] Int. Cl.⁵ .................. C07D 207/24; A61K 31/40
[52] U.S. Cl. .................. 514/409; 514/423; 514/424; 548/530; 548/543
[58] Field of Search .................. 548/543, 410, 530; 514/424, 423, 404

[56] References Cited

U.S. PATENT DOCUMENTS

| | | | |
|---|---|---|---|
| 3,975,399 | 8/1976 | DeFranco et al. | 260/326.2 |
| 4,452,807 | 6/1984 | Aschwanden et al. | 424/274 |
| 4,461,906 | 7/1984 | Aschwanden et al. | 548/406 |
| 4,800,212 | 1/1989 | Evans et al. | 514/424 |

FOREIGN PATENT DOCUMENTS 0221025  5/1987  European Pat. Off.
WO86/07054  12/1986  PCT Int'l Appl.

OTHER PUBLICATIONS

Mauger, A. B., J. Org. Chem. 46 (1981) 1032–1035.
Cocolas, G. H. et al., J. Am. Chem. Soc. 79 (1957) 5203–5205.
Delaney, N. G., et al., J. Am. Chem. Soc. 104 (1982) 6635–6641.
Hartwig, W., et al., J. Org. Chem., 52 (1987) 4352–4358.
Kende, A. S. et al., Tetrahedron Letters, 29 (1988) 2521–2524.

Primary Examiner—David B. Springer
Attorney, Agent, or Firm—Timothy J. Gaul

[57] ABSTRACT

Antihypercholesterolemic activity has been discovered in compounds of the formula

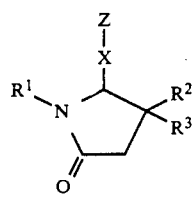

and pharmaceutically acceptable salts thereof, wherein: Z is

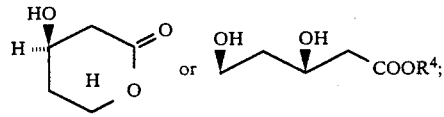

X is lower alkyl, lower alkenyl, or lower alkenyl;
$R^1$ is hydrogen, alkyl, alkenyl, aryl, alkylaryl, or substituted aryl having one or more substituents; and
one of $R^2$ and $R^3$ is hydrogen and the other is hydrogen, alkyl, alkenyl, aryl, alkylaryl or alkenyl aryl; or $R^2$ and $R^3$ are both lower alkyl; or $R^2$ and $R^3$ together complete a substituted or unsubstituted hydrocarbon ring that is cycloalkyl or cycloalkenyl with substituents as defined in the specification.

26 Claims, No Drawings

2-PYRROLIDONE SUBSTITUTED DIHYDROXY ALKANOIC, ALKENOIC AND ALKYNOIC ACIDS, COMPOSITIONS AND HMG-COA REDUCTASE INHIBITION THEREWITH

FIELD OF THE INVENTION

The present invention relates to 2-pyrrolidone substituted dihydroxy alkanoic, alkenoic and alkynoic acids that inhibit 3-hydroxy-3-methyl-glutaryl coenzyme A (HMG-CoA) reductase, an enzyme used in cholesterol biosynthesis. The compounds of this invention are, therefore, useful as antihypercholesterolemic agents.

BRIEF DESCRIPTION OF THE INVENTION

Antihypercholesterolemic activity has been discovered in a compound of the formula

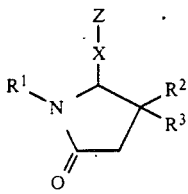

I and pharmaceutically acceptable salts thereof, wherein:
Z is

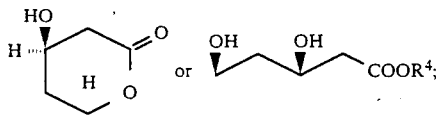

X is lower alkyl, lower alkenyl, preferably, trans-alkenyl, or lower alkynyl;

$R^1$ is hydrogen, alkyl, alkenyl, aryl, alkylaryl, or substituted aryl having substituents $R^5$ and $R^6$, one of $R^2$ and $R^3$ is hydrogen and the other is hydrogen, alkyl, alkenyl, aryl, substituted aryl having substituents $R^7$ and $R^8$, alkylaryl, or alkyl-substituted aryl having substituents $R^7$ and $R^8$; or $R^2$ and $R^3$ are both lower alkyl; or $R^2$ and $R^3$ together complete a hydrocarbon ring that is:
(1) cycloalkyl,
(2) cycloalkenyl,
(3) substituted cycloalkyl, having substituents $R^5$ and $R^6$,
(4) substituted cycloalkenyl having substituents $R^5$ and $R^6$;

$R^4$ is selected from:
(1) hydrogen,
(2) ammonium,
(3) mono-, di-, or trialkylammonium,
(4) alkali metal, such as lithium, sodium or potassium,
(5) alkyl,
(6) alkyl substituted with phenyl,
(7) alkylarylamine, and
(8) diarylalkylamine;

$R^5$ and $R^6$ are each independently selected from:
(1) alkyl,
(2) substituted alkyl having one or more substituents selected from:
(i) halogen,
(ii) nitro,
(iii) hydroxy,
(iv) alkoxy,
(v) alkoxycarbonyl,
(vi) acyl,
(vii) acyloxy,
(viii) cyano,
(ix) aryl,
(x) substituted aryl having substituents $R^7$ and $R^8$,
(xi) alkyl-$S(O)_n$,
(xii) dialkylamino,
(xiii) cycloalkyl-$S(O)_n$,
(xiv) aryl-$S(O)_n$,
(xv) substituted aryl-$S(O)_n$, having substituents $R^7$ and $R^8$, and
(xvi) oxo,
(3) alkyl-$S(O)_n$,
(4) cycloalkyl-$S(O)_n$,
(5) aryl-$S(O)_n$,
(6) substituted aryl-$S(O)_n$ having substituents $R^7$ and $R^8$,
(7) halogen,
(8) hydroxy,
(9) alkoxy,
(10) alkoxycarbonyl,
(11) acyloxy,
(12) aryl,
(13) substituted aryl having substituents $R^7$ and $R^8$,
(14) cycloalkenyl-$S(O)_n$, and
(15) hydrogen, $R^7$ and $R^8$ are each independently hydrogen, halogen, trifluoromethyl, alkyl, nitro, alkoxy, or cyano; and
n is 0, 1, or 2.

Formula I compounds inhibit cholesterol biosynthesis by competitive inhibition of HMG CoA reductase, which is a key enzyme in cholesterol biosynthesis.

DETAILED DESCRIPTION OF THE INVENTION

Definition of Terms

Listed below are definitions of various terms used to describe this invention. These definitions apply to the terms as they are used throughout the specification (unless otherwise limited in specific instances) either individually or as part of a larger group. Where exemplary and preferred groups are listed in any definition of a term, these groups are used to illustrate rather than limit the meaning of the term.

The term "alkali metal" refers to lithium, sodium, and potassium.

The term "alkyl" as employed herein by itself or as part of another group includes both straight and branched chain hydrocarbon groups, preferably of 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as substituted alkyl groups (wherein the group is attached by way of the alkyl portion rather than a substituent), including alkyl groups having one or two halo-substituents, such as fluorine, chlorine, bromine, iodine or CFs, an alkoxy substituent, an aryl substituent, an alkyl-aryl substituent, a haloaryl substituent, a cycloalkyl substituent or an alkylcycloalkyl substituent.

The terms "cycloalkyl" and "cycloalkenyl" by themselves or as part of another group refer to cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, or 1 or 2 lower alkoxy groups, wherein the group is attached by way of the cycloalkyl portion rather than a substituent.

The terms "alkenyl" and "alkynyl" refer to both straight and branched chain groups. Those groups having 2 to 10 carbon atoms are preferred. The terms "alkenyl" and "alkynyl" further include groups having one or two halo substituents, an alkoxy substituent, an aryl substituent, an alkyl-aryl substituent, a haloaryl substituent, a cycloalkyl substituent, or an alkylcycloalkyl substituent, wherein the groups are attached by way of the alkenyl or alkynyl portion rather than a substituent.

The terms "lower alkyl", "lower alkenyl", and "lower alkynyl" refers to such groups as defined herein having 1 to 4 carbon atoms.

The terms "halogen" and "halo" refer to fluorine, chlorine, bromine and iodine, as well as —CF₃.

The terms "aryl" or "Ar" refer to monocyclic or bicyclic aromatic groups containing from 6 to 10 carbons in the ring portion, such as phenyl, naphthyl, substituted phenyl or substituted naphthyl (attached by way of the aryl portion rather than substituent) wherein the substituent on either the phenyl or naphthyl may be 1 or more lower alkyl groups, 1 or more halogens (Cl, Br or F), and/or 1 or more lower alkoxy groups or combinations thereof.

The terms "aralkyl", "aryl-alkyl", "alkyl-aryl" or "aryl-lower alkyl" refer to hydrocarbon groups having both aryl and alkyl portions as those terms are defined herein, wherein such groups are attached by way of the alkyl portion and include aryl (substituted alkyl), (substituted aryl) alkyl, and arylcycloalkylalkyl.

The term "acyl" refers to all organic moieties that may be derived from an organic acid (i.e., a carboxylic acid) by exchange of the hydroxyl group; i.e., compounds of the partial formula

wherein R is alkyl, aryl, aralkyl, amino, dialkylamino, alkylarylamino, diarylamino, alkoxy, cycloalkyl, aryloxy, alkenyl, cycloalkenyl, cyclohexadienyl, or alkyl, alkenyl, or aryl substituted with one or more halogen, cyano, nitro, mercapto, alkylthio or cyanomethylthio groups.

Use and Utility

The compound of formula I of the invention will be formulated with a pharmaceutical vehicle or diluent. The pharmaceutical composition can be formulated in a classical manner utilizing solid or liquid vehicles or diluents and pharmaceutical additives of a type appropriate to the desired mode of administration. The compounds can be administered by an oral route in the form of tablets, capsules, granules or powders, for example, or by a parenteral route in the form of injectable preparations.

A typical capsule for oral administration contains active ingredients (25 mg), lactose (75 mg) and magnesium stearate (15 mg). This mixture is passed through a 60-mesh sieve and packed into a No. 1 gelatin capsule.

A typical injectable preparation is produced by asceptically placing 25 mg of a water soluble salt of sterile active ingredient into a vial, then asceptically freeze-drying and sealing the vial. For use, the contents of the vial are mixed with 2 ml of physiological saline, to produce an injectable preparation.

The compounds of the invention inhibit HMG-CoA reductase and, therefore, cholesterol biosynthesis. Such compounds are useful in treating:
(1) atherosclerosis (to inhibit progression of disease),
(2) hyperlipidemia (to inhibit development of atherosclerosis), and
(3) nephrotic hyperlipidemia.

In addition, the compounds of the invention increase plasma high-density lipoprotein cholesterol levels.

As HMG-CoA reductase inhibitors, the compounds of the invention may also be useful in inhibiting formation of gallstones and in treating tumors. In addition, the compounds of the invention may be useful in elevating high density lipid (HDL) cholesterol levels while lowering low density lipid (LDL) cholesterol and serum triglyceride levels.

The compounds of the invention may also be employed in combination with:
(1) an antihyperlipoproteinemic agent (e.g., probucol),
(2) one or more serum cholesterol-lowering agents (e.g., "Lopid" ™, or gemfibrozil),
(3) bile acid sequestrants (e.g., cholestyramine),
(4) colestipol,
(5) DEAE-Sephadex
(6) niacin,
(7) clofibrate,
(8) nicotinic acid and its derivatives,
(9) neomycin,
(10) p-aminosalicyclic acid,
(11) lovastatin, pravastatin, visinolin (velostatin, symvastatin or synvinolin) and the like, and
(12) one or more squalene synthetase inhibitors.

The above compounds to be employed in combination with the invention will be used in amounts indicated in the Physicians' Desk Reference (PDR).

The dose to be administered depends on the unitary dose, the symptoms, and the age and body weight of the patient. A dose for adults is preferably between 20 and 2,000 mg per day, which can be administered in a single dose or in one to four divided doses per day.

The compounds of this invention also have useful antifungal activities. For example, they may be used to control strains of Penicillium sp., *Aspergillus niger*, *Cladosporium* sp., *Cochliobolus miyabeorus* and *Helminthosporium cynodnotis*. For those utilities, they are first admixed with suitable formulating agents, powders, emulsifying agents or such solvents as aqueous ethanol, and then sprayed or dusted on the plants to be protected.

Process of Preparation

Compounds of this invention may be prepared by the following exemplary processes.

Compound I may be prepared from the aldehyde compound of the formula

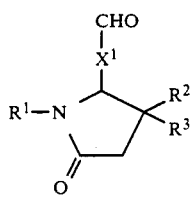

II wherein $X^1$ is a bond or lower alkynyl. Compound II is novel and forms an integral part of this invention.

Method A

Method A may be used when X in compound I is lower alkyl or lower alkenyl.

Following procedures similar to those described in A. B. Mauger, J. Organic Chem., 46, 1032 (1981), the dialkylacetamidomalonate compound

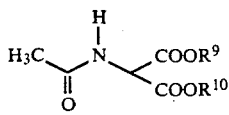   III (wherein $R^9$ and $R^{10}$ are lower alkyl) may be reacted with an unsaturated ester $R^2R^3$—Y—COOR$^{11}$   IVa (wherein Y is alkenyl and $R^{11}$ is lower alkyl) in the presence of a catalyst MOR$^{12}$   IVb (wherein M is alkali metal and $R^{12}$ is lower alkyl) in an organic solvent (e.g., ethanol) under reflux conditions to yield the pyrrolidone diester

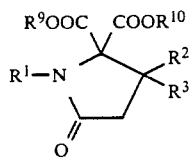   V wherein $R^1$ is hydrogen. This compound may be alkylated by treatment with a base (e.g., sodium hydride) and an alkyl halide or alkenyl halide or aryl-alkylhalide in an organic solvent (e.g., dimethylformamide) to yield compound V wherein $R^1$ is alkyl, alkenyl, or alkylaryl. Alternatively, compound V wherein $R^1$ is hydrogen can be arylated by treatment with an aryl halide (e.g., phenyl bromide) in the presence of a catalyst such as cuprous oxide to yield compound V wherein $R^1$ is aryl or substituted aryl.

Pyrrolidone diester compound V where $R^1$ is a group other than hydrogen may be selectively hydrolyzed at one ester group, for example, by treatment with an alkali metal hydroxide (e.g., sodium hydroxide) in an organic solvent (e.g., ethanol). Subsequent heating for decarboxylation provides the monoester compound

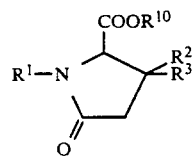   VI wherein $R^1$ is a group other than hydrogen as chromatographically separable cis and trans isomers when one of $R^2$ or $R^3$ is hydrogen, or as a single isomer when $R^2$ and $R^3$ are either the same or together form part of a cycloalkyl group.

Alternatively, compound V wherein $R^1$ is hydrogen may be hydrolyzed and decarboxylated by treatment with an alkali metal hydroxide (e.g., sodium hydroxide) in an organic solvent (e.g., ethanol) to yield compound VI wherein $R^1$ is only hydrogen. That compound can then be alkylated or arylated as described above to provide a mixture of separable stereoisomers of compound VI wherein $R^1$ is alkyl, alkenyl, aryl, substituted aryl, or alkylaryl.

Compound VI may be reduced by treatment with an alkali borohydride (e.g., lithium borohydride) in the presence of a lower alkyl alcohol such as methanol in an organic solvent (e.g., tetrahydrofuran) to yield an alcohol compound

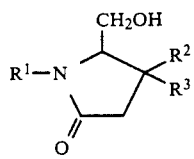   VII wherein $R^2$ and $R^3$ are each independently hydrogen, alkyl, alkenyl, aryl or aralkyl.

Compound VII may be treated with conventional oxidizing agents (Dess Martin Periodinane is preferred) in organic solvents (e.g., methylene chloride, containing some t-butanol as catalyst) to yield aldehyde compound II wherein $X^1$ is a bond.

Alternatively, compound IVa may be first reduced with, for example, diisobutylaluminum hydride in an organic solvent such as toluene to form the unsaturated alcohol $R^2R^3$—Y—CH$_2$OH.   VIII Alcohol compound VIII may be subjected to a Claisen rearrangement by heating with an orthoester (e.g., triethyl orthoacetate) and an organic acid (e.g., propionic acid) under reflux conditions, followed by hydrolysis with an alkali metal hydroxide in an organic solvent (e.g., methanol) in water to yield the acid compound

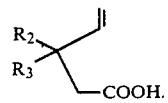   IX

Compound IX may be converted to the acid halide by treatment with, for example, oxalyl chloride in the presence of dimethylformamide in methylene chloride. The acid chloride may be reacted with an amine (e.g., p-fluoroaniline) in an appropriate organic solvent (e.g., methylene chloride) in the presence of a trialkylamine (e.g., triethylamine) to yield an unsaturated amide

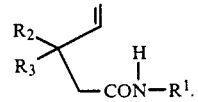   X

Amide compound X may be treated with such a reactant as osmium tetroxide in the presence of N-methylmorpholine oxide to regenerate osmium tetroxide in an aqueous inert solvent (e.g., acetone) to yield the diol compound

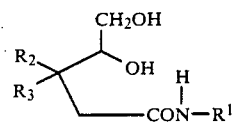

Compound XI may then be reacted with in sequence:
1. A sulfonyl halide (e.g., p-toluene-sulfonyl chloride) and an acid denaturant (e.g., pyridine, dimethylaminopyridine) at about 0° C., and
2. an organic base (e.g., potassium t-butoxide) in an appropriate organic solvent (e.g., dimethylformamide) at about 0° to 25° C.

to yield compound VII (as a mixture of separable stereoisomers when $R^2$ and $R^3$ are not identical). Compound VII may be treated as described above to yield compound II wherein $X^1$ is a bond. Compound II wherein $X^1$ is a bond is reacted with the optically active phosphonate compound

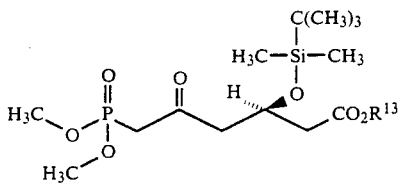

wherein $R^{13}$ is lower alkyl or phenyl-substituted lower alkyl. Compound XII may be prepared following procedures described in U.S. Pat. No. 4,804,770, issued Feb. 14, 1989. Compound II may be reacted with compound XII in a relatively straightforward Horner-Emmons reaction using a catalyst such as 1,8-diazabicyclo [5,4,0] undec-7-ene, a salt such as lithium chloride, and an organic solvent such as acetonitrile to yield the unsaturated ketone of the formula

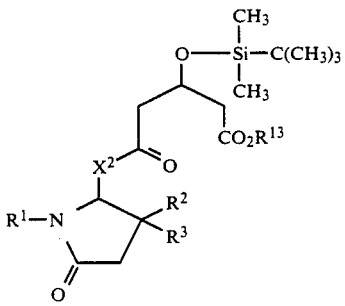

wherein $X^2$ is alkenyl (see also U.S. patent application Ser. No. 182,710, filed Apr. 18, 1988).

Compound XIII is then deprotected by acid treatment (e.g., hydrofluoric acid) in an organic solvent (e.g., acetonitrile) to yield an alcohol

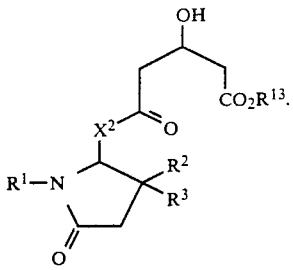

Compound XIV is reduced by, for example, sodium borohydride in the presence of triethylborane in an organic solvent (e.g., tetrahydrofuran) in admixture with an alcohol solvent (e.g., methanol) at about −78° C. to form a compound of formula I wherein $X^2$ is lower alkenyl and $R^4$ is lower alkyl. This compound may be hydrolyzed with an alkali metal hydroxide (e.g., lithium hydroxide) in an organic solvent to form a compound of formula I wherein X is alkenyl, Z is

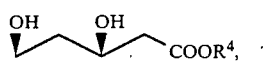

and $R^4$ is alkali metal.

The latter compound may be converted by conventional means to form compound I wherein $R^4$ is hydrogen. The compound wherein $R^4$ is hydrogen may be aminated by conventional means to form the formula I compounds wherein $R^4$ is ammonium, dialkylammonium, alkylarylammonium, or diarylalkylammonium or triarylammonium. To form a formula I compound wherein X is alkyl, the associated compound wherein X is alkenyl and $R^4$ is alkali metal or lower alkyl may be hydrogenated in the presence of a catalyst (e.g., palladium on carbon) in an organic solvent (e.g., ethyl acetate, methanol) or mixtures thereof.. To form- compound I where Z is the lactone

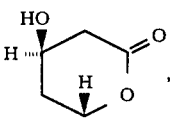

the associated open-chain acid may be, for example, heated in toluene to about 100° to 130° C. or treated with a catalytic amount of trifluoroacetic acid at about ambient temperature in an organic solvent (e.g., tetrahydrofuran).

Method B

Formula I compounds wherein X is alkynyl may be prepared by Method B.

Following procedures similar to those disclosed in U.S. patent application Ser. No. 182,710, filed Apr. 18, 1988, a compound of formula 11 wherein $X^1$ is a bond may be treated with diazomethyl diethylphosphonate and potassium t-butoxide in an organic solvent such as tetrahydrofuran at a temperature of about −45° C. to yield

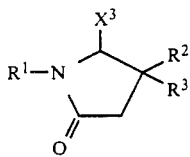

wherein $X^3$ is alkynyl. Compound XV may then be reacted with an organometallic base (e.g., n-butyl lithium) and paraformaldehyde in an organic solvent (e.g., tetrahydrofuran) to provide the acetylenic alcohol

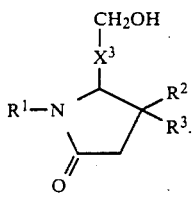

Compound XVI may be oxidized by, for example, Dess Martin periodinane and t-butanol in methylene chloride to yield the corresponding aldehyde compound II wherein $X^1$ is alkynyl.

Compound II wherein $X^1$ is alkynyl may be reacted with the known dianion

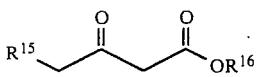

wherein $R^{15}$ and $R^{16}$ are lower alkyl by reaction successively with an inorganic base such as sodium hydride and an organometallic base such as n-butyl lithium to produce a diastereomeric mixture of the ketol

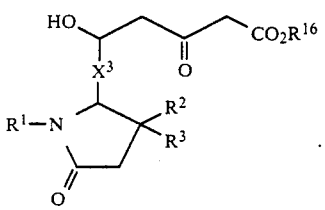

Compound XVIII may be reduced by, for example, sodium borohydride in the presence of triethylborane to yield compounds of formula I wherein $R^4$ is lower alkyl and X is alkynyl. This compound may be treated as described in Method A hereof to produce formula I compounds wherein X is alkynyl, Z may be lactone, and $R^4$ is other than lower alkyl.

SPECIFIC EMBODIMENTS

The following working examples represent specific, preferred embodiments of the invention. Within each example, the preparation of each intermediate is provided just below the name of that intermediate. As a shorthand reference, the compound prepared in part 1-A will be referred to as "compound 1-A" or "intermediate 1-A"; likewise for the compounds prepared in parts 1-B, 1-C, etc. Except where otherwise indicated, all temperatures are given in degrees Celsius (° C.). These examples are meant to be illustrative rather than limiting; this invention is limited only by the claims appended hereto.

EXAMPLE 1

(3R,5S,6E,cis)-3,5-Dihydroxy-7-[3-methyl-5-oxo-1-(phenylmethyl)-2-pyrrolidinyl]-6-heptenoic acid, methyl ester 1-A. 5,5-Diethoxycarbonyl-4-methyl-2-pyrrolidinone Sodium (400 mg, 17.4 mmol) was dissolved in absolute ethanol (100 ml) freshly distilled from Mg turnings. Diethyl acetamidonmalonate (21.7 g, 100 mmol, Aldrich Chem. Co.) was added under stirring followed by ethyl crotonate (17.1 g, 150 mmol) in the course of 5.0 minutes at ambient temperature under an atmosphere of nitrogen. After 15 minutes, the mixture was refluxed for 20 hours. It was then neutralized by the addition of acetic acid (to pH of about 7.0) and the ethanol was evaporated in vacuo. The residue was then steam-distilled for 1.0 hour to remove the volatile materials and the distillate was discarded. The pot residue was saturated with salt and was extracted with ethyl acetate (3×120 ml). The extracts were combined, dried (anhydrous magnesium sulfate) and was evaporated in vacuo to leave a solid residue (22 g). This was crystallized once from ethyl acetate-hexane to afford the title compound 1-A as colorless needles (15.5 g, 70%). Melting point 75°–77° (melting point 76°–78° from water, yield=88%; see Cocolas and Hartung, J. Amer. Chem. Soc., 79, 5203 (1957)). The $^1$H and $^{13}$C-NMR spectra were consistent with the structure.

The reaction was subsequently repeated on 1½ scale to afford 26.5 g more of material. The yield in this preparation was 73%.

1-B. cis-5-Ethoxycarbonyl-4-methyl-2-pyrrolidinone and

1-C. trans-5-Ethoxycarbonyl-4-methyl-2-pyrrolidinone

To a solution of compound 1-A (36.45 g, 150 mmol) in ethanol (150 ml) was added 1.0N sodium hydroxide (150 ml). After 24 hours, 1.0N hydrochloric acid (150 ml) was added and the solution was evaporated. The residue was treated with warm ethanol (175 ml) and was filtered to remove the sodium chloride. After evaporation, the residue was heated in an oil bath at 150° for 30 minutes, cooled, dissolved in ether (100 ml) filtered and evaporated. The residue was then distilled at boiling point 125°–135° at about 0.5 mm Hg to afford a mixture (24.3 g, 95%) of compounds 1-B and 1-C as a colorless oil. According to Mauger, J. Org. Chem., 46, 1032 (1981), this was a 1:1 mixture of compounds 1-B and 1-C which are difficult to separate by column chromatography on silica gel. Three successive crystallizations respectively from 140 ml, 70 ml and 140 ml of ether at −15° to −20° C., with $^1$H and $^{13}$C-NMR monitoring, gave the homogeneous specimen of compound 1-B as prisms (6.2 g, 25.5%).

Melting point 58°–60° (according to Mauger: 77.5 to 78° C., needles from ether). This specimen of compound 1-B was homogeneous from its $^1$H and $^{13}$C-NMR spectra. Three attempted crystallizations of the material in the mother liquor from ether gave only a mixture of compounds 1-B and 1-C.

1-D. N-Benzyl-cis-5-ethoxycarbonyl-4-methyl-2-pyrrolidinone

1-E. N-Benzyl-trans-5-ethoxycarbonyl-4-methyl-2-pyrrolidinone

An approximately 7:3 mixture of compounds 1-B and 1-C (3.07 g, 17.95 mmol) in dry dimethylformamide (35 ml) was stirred in an ice-bath for 1½ hours with 60% sodium hydride-paraffin (800 mg, 20 mmol). A solution of benzyl bromide (3.76 g, 22 mmol) in dry dimethylformamide (5.0 ml) was then added dropwise. After 45 minutes, the mixture was added to dilute brine (150 ml) and extracted with ether (3×60 ml). The extracts were combined, washed with dilute-brine (3×20 ml), dried (anhydrous magnesium sulfate) and evaporated to afford the crude product as an oil. This product was chromatographed on a column of silica gel (Baker 60-200, 70 g), eluting the column with methylene chloride-hexane (1:1), methylene chloride and methylene chloride-ethyl acetate (7:3) to afford a mixture of compounds 1-D and 1-E as an oil (3.92 g, 84%) which later solidified. The $H^1$ and $C^{13}$ NMR spectra showed that this was an approximately 7:3 mixture of compounds 1-D and 1-E.

1-F. cis-(N-Benzyl-4-methyl-2-pyrrolidonyl)-5-methanol and

1-G. trans-(N-Benzyl-4-methyl-2-pyrrolidonyl)-5-methanol

A solution of the above mixture of compounds 1-D and 1-E (2.3 g, 8.81 mmol) in a mixture of dry tetrahydrofuran (50 ml) and methanol (2.7 ml) was stirred with lithium borohydride (1.5 g, 68 mmol) under an atmosphere of nitrogen for 18 hours. Water (10 ml) was added, followed after a few minutes by hydrochloric acid (70 ml). After stirring for 30 minutes, the mixture was diluted with brine (50 ml) and extracted with ethyl acetate. The extracts were combined, washed with brine, dried (magnesium sulfate) and evaporated to afford the crude product as a thick oil (1.67 g, 91.6%). The $H^1$ and $C^{13}$ NMR spectra showed that this was an approximately 7:3 mixture of 1-F and 1-G; these were separable by flash chromatography on silica gel using ethyl acetate-hexane (80:2) for elution. Reduction of compound 1-D (contaminated with about 5% of the trans-ester 1-E) under similar conditions gave compound 1-F as a solid contaminated with about 5% of compound 1-G. The isomers 1-F and 1-G could be readily distinguished by their $H^1$ and $C^{13}$- NMR spectral data and thin layer chromatography behavior. The separation of isomers, however, was deferred until the next step.

1-H. cis-N-Benzyl-3-methyl-4-formyl-2-pyrrolidinone and

1-I. trans-N-Benzyl-3-methyl-4-formyl-2-pyrrolidinone

A solution of the above mixture of compounds 1-F and 1-G (1.67 g, 763 mmol) in dichloromethane (20 ml) was stirred under an atmosphere of nitrogen at ambient temperature with Dess-Martin Periodinane (3.79 g, 8.8 mmol) and t-butanol (661 mg, 8.8 mmol) for 2.0 hours. It was then diluted with dichloromethane (20 ml), a solution of sodium bicarbonate (5.88 g, 70 mmol) in 0.5M sodium thiosulfate solution (100 ml) was cautiously added, and the mixture was stirred vigorously for 30 minutes. The clear dichloromethane layer was then separated, washed once with brine, dried (anhydrous magnesium sulfate) and was evaporated to afford a mixture of compounds 1-H and 1-I as an oil (1.6 g). This oil was subjected to a column chromatography on Baker 60-200 silica gel (50 g), eluting the column successively with methylene chloride-hexane (1:1), methylene chloride and methylene chloride:ethyl acetate (8:2) to isolate the less polar compound 1-H (938 mg, 56.6%), and more polar compound 1-I (470 mg, 28.4%) as oils. The isomeric compounds 1-H and 1-I could be readily distinguished from their $H^1$ and $C^{13}$ NMR spectra and thin layer chromatography behavior.

Oxidation of essentially homogeneous alcohol 1-F under similar conditions gave essentially homogeneous compound 1-H (thin layer chromatography, $H^1$ and $C^{13}$ NMR data); further, reduction of pure compound 1-H with sodium borohydride in methanol gave pure compound 1-I uncontaminated with compound 1-H, thus establishing the stereochemical integrity of these products

1-J. 3-(t-Butyldimethylsilyloxy)glutaric acid, diethyl ester

To a solution of imidazole (40.85 g, 600 mmol) in dry methylene chloride (300 ml) was added dropwise a solution of t-butyldimethylsilyl chloride (45.2 g, 300 mmol) in dry methylene chloride (100 ml). After 15 minutes, the solution was treated dropwise over a 40-minute period with a solution of diethyl 3-hydroxyglutarate (40.8 g, 200 mmol) in methylene chloride (100 ml). After stirring at room temperature under argon for 18 hours, the mixture was washed with water and saturated sodium chloride solution, dried over sodium sulfate and evaporated. The crude product (73.04 g) was purified by chromatography on Merck silica gel (4000 ml), eluting with ether-hexane (1:9) to give intermediate compound 1-J (about 65 g, theory 63.6 g) as a colorless oil. Thin layer chromatography: (ethyl acetate-hexane 1:1) Rf-0.46 (Rf of 3-hydroxyglutarate was 0.20). $C^{13}$-NMR (15 MHz, $CDCl^3$) −5.02 ppm, 14.00, 17.77, 25.50, 42.51, 60.24, 66.28, 170.78.

1-K. 3-(t-Butyldimethylsilyloxy)glutaric anhydride

A solution of silyl-ether compound 1-I (theory 63.6 g, 200 mmol) in methanol (200 ml) was treated with sodium hydroxide pellets (16.0 g, 400 mmol) and stirred at room temperature under argon for 18 hours. The cloudy yellow solution was evaporated to dryness and dried in vacuo to give the disodium salt as a pale yellow solid. The disodium salt (42.1 g) was suspended in benzene (400 ml), treated with acetic anhydride (200 ml) and refluxed under argon for 1.5 hours. The brown mixture was concentrated in vacuo and the residue partitioned between ethyl acetate and half-saturated sodium hydrogen carbonate. The organic phase was washed with half-saturated sodium bicarbonate and saturated sodium chloride solutions, dried over sodium sulfate and evaporated to give the crude anhydride intermediate 1-K as a brown solid. The crude product was taken up in ether, treated with Darco ® (3 g), filtered through Celite ® and evaporated. The crystalline residue was triturated with cold hexane to give pure anhydride compound 1-K (33.26 g, 68% overall from compound 1-J) as white plates. Melting point 77°–78° C., $C^{13}$-NMR (15 MHz, $CDCl_3$) −5.22 ppm, 17.64, 25.31, 38.88, 61.87, 165.26.

1-L.
4-[S-(2-Phenethylamino)carbonyl]-3-[(t-butyl-dimethylsilyl)-oxy]-butanoic acid A solution of anhydride compound 1-K (7.32 g, 30.0 mmol) in dry toluene (120 ml) was cooled to −78° C. (dry ice-ethyl hydroxide) under argon (some compound 1-K precipitates). To this mixture was added dropwise triethylamine (4.2 ml, 30.0 mmol) followed by S(−)α-methyl benzylamine (4.2 ml, 32.6 mmol). After stirring at −78° C. for 4.5 hours, the cooling bath was removed, the mixture allowed to warm to room temperature, and stirred for one hour. The mixture was partitioned between ethyl acetate (100 ml) and tetrahydrofuran (50 ml)/5% potassium hydrogen sulfate (175 ml). The organic phase was washed with 5% potassium hydrogen sulfate and saturated sodium chloride solutions, dried over sodium sulfate and evaporated to give crude intermediate compound 1-L as a white semi-solid. Esterification of a 25 mg sample of the crude product with diazomethane gave a 79:21 mixture of (3S,1'S): (3R,1'S) methylesters as determined by $^1$H-NMR (270 MHz, CD$_3$CN). Thin layer chromatography: (ether-hexane; 2:1) Rf=0.37 (major, 3S,1'S), 0.29 (minor, 3R,1'S). $^1$H-NMR (3S,1'S) δ 0.08 ppm (3H,S), 0.10 (3H,S), 0.86 (9H,S). $^1$H-NMR (3R,1'S) δ 0.03 ppm (3H,S), 0.06 (3H,S), 0.79 (9H,S).

The crude acid was triturated with cold ether to give (3S,1'S) intermediate 1-L (8.160 g, 74.5%) as white crystals which showed only a trace of the 3R,1'S-isomer after esterification with diazomethane. Evaporation of the mother liquor gave 2.756 g of the 3R,1'S-isomer as a thick oil.

The above experiment was repeated exactly 76%) and (3R,1'S) compound 1-L (2.654 g). The two batches of the crystalline isomer (total: 16.435 g) were combined and recrystallized from ethyl acetate-hexane to give pure (3S,1'S) compound 1-L (15.790 g, 72%) as white plates. Melting point: 175.5°–176.5° C. [α]=−68.4° (c=1.02, methanol). Esterification of the recrystallized material with diazomethane showed no trace of the 3R,1'S-isomer by thin layer chromatography or 270 MHz NMR.

1-M.
4-[S-(2-Phenethylamino)carbonyl]-3-[(t-butyl-dimethylsilyl)-oxy]-butanoic acid, methylester A solution of acid compound 1-L (15.365 g, 42.1 mmol) in dry dimethylformamide (50 ml) was treated with powdered potassium bicarbonate (6.30 g, 63.0 mmol) and methyl iodide (3.90 ml, 62.6 mmol) and stirred at room temperature under argon for 18 hours. The mixture was then partitioned between ethyl acetate (250 ml) and water (150 ml); the organic phase was washed with water (3×75 ml) and saturated sodium chloride solution, dried over sodium sulfate and evaporated to give crude compound 1-M (16.56 g, theory: 15.95 g) as a colorless oil. Thin layer chromatography (ether:hexane; 2:1) showed a single spot, Rf=0.37.

1-N.
3R-[4-(Methoxycarbonyl)]-3-[(t-butyldimethylsilyl)-oxy]-butanoic acid A suspension of anhydrous sodium acetate (10.5 g, 128 mmol) in a solution of crude amide-ester compound 1-M (16.56 g, theory: 15.95 g, 42.1 mmol) in dry carbon tetrachloride (100 ml) at 0° C. (ice bath) under argon was treated with 7.8M nitrogen tetroxide/carbon tetrachloride (75 ml, prepared by passing nitrogen tetroxide in carbon tetrachloride at 0° C., concentration determined iodometrically) in about 20 ml portions. After stirring at 0° C. for 3 hours, the cold mixture was partitioned between methylene chloride-ice and water. The organic phase was dried over sodium sulfate and evaporated at room temperature to give the crude product N-nitrosoamide as a bright yellow oil. Thin layer chromatography (ether-hexane; 2:1) found Rf=0.70 (Rf of compound 1-M=0.37).

The crude N-nitrosoamide was immediately taken up in dioxane (100 ml) and heated to 65°–75° C. (bath temperature) under argon for 2.5 hours. Vigorous N$_2$ evolution was observed and the yellow color of the solution gradually faded until the solution was nearly colorless. Evaporation of the solution gave about a 1:1 mixture of acid compound 1-N and its corresponding α-methylbenzyl ester. Thin layer chromatography (methylene chloride-hexane; 3:1): Rf (acid)=0.05, Rf (ester)=0.37, (Rf of N-nitrosoamide=0.56).

The mixture of acid compound 1-N and its α-methylbenzyl ester was taken up in methanol (100 ml), treated with 20% palladium on carbon (1.0 g) and stirred under a hydrogen atmosphere (balloon) for 2 hours. The mixture was filtered through Celite and evaporated to dryness to give crude compound 1-N (11.6 g, 100%) as a colorless oil, which solidified in the refrigerator. Thin layer chromatography (methanol-methylene chloride; 1:9) found Rf=0.51.

1-O.
(R)-6-(Dimethoxyphosphinyl)-3-[[(1,1-dimethylethyl)-dimethylsilyl]oxy]-5-oxohexanoic acid, methylester To a solution of dimethyl methylphosphonate (18.8 g, 152 mmol) in dry tetrahydrofuran (200 ml) at −78° C. under argon was added 1.6M n-butyl lithium/hexane (92 ml, 147 mmol) via syringe over a period of ten minutes. The resulting mixture was stirred at −78° C. for 45 minutes, during which time a white precipitate developed. To the resulting solution was added a solution of the crude acid compound 1-N (11.6 g, 42 mmol) in tetrahydrofuran (50 ml) dropwise over a period of about 15 minutes. The resulting mixture was stirred at −78° C. for one hour and then quenched by the dropwise addition of saturated ammonium chloride solution (20 ml). The mixture was allowed to warm to room temperature and partitioned between ethyl acetate and 5% potassium hydrogen sulfate. The organic phase was washed with saturated sodium chloride solution, dried over sodium sulfate and evaporated to give the crude keto-phosphonate acid as a colorless oil. Thin layer chromatography (methanol-methylene chloride; 1:9): Rf=0.44 (Rf of compound 1-N=0.51).

A solution of the crude acid in ether (75 ml) at 0° C. (ice bath) was treated with diazomethane/ether (prepared from 15.0 g 1-methyl-3-nitro-1-nitroso guanidine and 50 ml 40% potassium hydroxide/150 ml ether) in portions until the yellow color of excess diazomethane persisted. Acetic acid was added to discharge the excess diazomethane and the solution was evaporated to dryness. The crude methyl ester was purified by flash chromatography on LPS-1 (150 g) eluting with acetone-hexane (2:8) to give pure keto-phosphonate compound 1-O (10.521 g, 65% overall from compound 1-N) as a pale yellow, viscous oil. Thin layer chromatography: (acetone-hexane; 4:6) Rf=0.31. $^1$H-NMR (270 MHz, CD$_3$CN) 0.0 ppm (Ref., 6H,S), 0.78 (OH,S), 2.33 (1H,q,J=15, 7 Hz), 2.48 (1H,q,J=15, 5 Hz), 2.80 (2H, septet), 3.06 (2H,d,J=23 Hz), 3.56 (3H,S), 3.64 (6H,d,J=11 Hz), 4.46 (1H,quintet, J=5–6 Hz).

1-P.
(3R,6E,Cis)-3-[[(1,1-dimethylethyl)-dimethylsilyl]oxy]-5-oxo-7-[3-methyl-5-oxo-1-(phenylmethyl)-2-pyrrolidinyl]-6-heptenoic acid, methylester A mixture of aldehyde compound 1-H (502 mg, 2.31 mmol), the chiral phosphonate compound 1-O (0.96 g, 2.5 mmol) and lithium chloride (127.2 mg, 3.0 mmol) in dry acetonitrile (3.5 ml) was stirred at ambient temperature under an atmosphere of nitrogen and a solution of 1,8 diazalbicyclo -(5.4.0) undec-7-ene (351 mg, 2.31 mmol) in dry acetonitrile (1.0 ml) was added. After 2¼ hours, the turbid mixture was added into a 5% potassium hydrogen sulfate solution (30 ml) and was extracted with ethyl acetate (3×20 ml). The extracts were combined, washed with dilute brine, dried (anhydrous magnesium sulfate) and evaporated to afford the crude product as an oil. This product was chromatographed on a column of Baker 60-200 mesh silica gel (25 g) eluting the column with hexane-methylene chloride (1:1), methylene chloride and methylene chloride-ethyl acetate (9:1) to isolate compound 1-P as a homogeneous (thin layer chromatography: silica gel, ethyl acetate; Rf: 0.7) oil (922 mg, 84.6%) with consistent $H^1$-and $C^{13}$-NMR spectra data. On the basis of the $C^{13}$-NMR spectrum, this was a mixture of two chiral diastereomers (about 1:1) which were not readily separable by silica gel chromatography. None of the isomeric cis-substituted pyrrolidone products (see Example 2) could be detected by thin layer chromatography or examination of the $H^1$ and $C^{13}$ NMR spectra.

1-Q.
(3R,6E,Cis)-3-hydroxy-5-oxo-7-(3-methyl-5-oxo-1-(phenylmethyl)-2-pyrrolidonyl]-6-heptenoic acid, methylester A solution of compound 1-P (460 mg, 0.97 mmol) in acetonitrile (4.0 ml) was stirred with 48% hydrofluoric acid (0.25 ml) for 1½ hours at ambient temperature. The mixture was then added into brine (20 ml) and extracted with methylene chloride. The extracts were combined, washed with a dilute sodium bicarbonate solution and brine, dried (anhydrous magnesium sulfate) and evaporated to afford the crude product as an oil. This product was chromatographed on a column of Baker 60-200 silica gel (25 g), eluting the column with methylene chloride, methylene chloride-ethyl acetate (8:2) and ethyl acetate to isolate compound 1-Q as a homogeneous (thin layer chromatography, silica gel; ethyl acetate; Rf 0.25, uv; Ce-Mo-H$_2$SO$_4$-heat) oil (289 mg, 83%) with consistent $H^1$ and $C^{13}$ NMR spectral data. It was a mixture of chiral diastereomers (about 1:1) which were not readily separable by silica gel chromatography.

1-R.
(3R,5S,6E,Cis)-3,5-dihydroxy-7-[3-methyl-5-oxo-1-(phenylmethyl)-2-pyrrolidinyl]-6-heptenoic acid, methylester A solution of compound 1-Q (289 mg, 0.8 mmol) in dry tetrahydrofuran (2.0 ml) containing pivalic acid (5.0 mg) and 1.0M triethyl borane in tetrahydrofuran (1.2 ml) was stirred under an atmosphere of nitrogen at ambient temperature for 20 minutes. It was then cooled to −78° in a dry ice-acetone bath and sodium borohydride (42 mg, 1.1 mmol) was added, followed dropwise by dry methanol (1:1 ml) in the course of 3.0 minutes. After 1.0 hour, a solution of 30% hydrogen peroxide (1.6 ml) in water (30 ml) was cautiously added, the mixture was warmed up to ambient temperature and was stirred for 25 minutes. It was then added into brine (20 ml) containing 1.0 N hydrochloric acid (92.0 ml) and extracted with ethyl acetate (3×20 ml). The extracts were combined, washed with a dilute sodium bicarbonate solution and brine, dried (magnesium sulfate anhydrous) and was evaporated to afford the crude product as an oil. This was chromatographed on a column of Baker 60-200 silica gel (15 g) eluting the column with methylene chloride, ethyl acetate (1:1), and ethyl acetate to afford homogeneous (thin layer chromatography: Rf=0.25, ethyl acetate, methanol in a ratio of 95:5 with ceric sulfate+ammonium molybdate +H$_2$SO$_4$ with heat for visualization referred to as "Ce-Mo-H$_2$SO$_4$-heat" in all subsequent examples) Example 1 as an oil (219 mg, 75.2%) with consistent $H^1$ and $C^{13}$ NMR spectral data.

EXAMPLE 2

(3R,5S,6E,cis)-3,5-Dihydroxy-7-[3-methyl-5-oxo-1-(phenylmethyl)-2-pyrrolidinyl]-6-heptenoic acid, monolithium salt A solution of Example 1, compound 1-R (219 mg, 0.601 mmol) in tetrahydrofuran (3.0 ml) was stirred with 1.0 N lithium hydroxide (0.65 ml) under an atmosphere of nitrogen at ambient temperature for 40 minutes. The mixture was then concentrated in vacuo, the residue was dissolved in distilled water (3.0 ml) and was applied on a column of HP-20 resin (3½"×1¼"). The column was eluted successively with deionized water (250 ml) and methanol-water (2:8; 200 ml). The methanol-water eluate was concentrated in vacuo and lyophilized to afford the analytical specimen of Example 2 as a colorless fluffy powder (188 mg, 88.7%) with consistent IR and $H^1$-NMR spectral data.

Analysis calculated for $C_{19}H_{24}NO_5Li$; 1.04 water (MW=353.35/372.04): C, 61.33: H, 7.06; N, 3.77%. Found: Cl, 61.42; H, 6,96; N, 3.75%.

IR spectrum (KBr): $\mu_{max}$ 3405–3420 (Cm$^{-1}$ (strong, OH), 1664 cm$^{-1}$ (strong, C=O, amide), 1585, 1422 Cm$^{-1}$ (strong, C=O, —COO)—.

$H^1$-NMR Spectrum (DMSO-d$_6$, Fx-270): δ 0.90 (3H, 2 doublets, J=∼8.0, H$_{19}$), ∼3.4 (m, H8), ∼3.75 (q, 1H, H3 or H5), ∼3.75, 4.75 (2 quarters, 1H each, H$_{12}$), 4.15 (q, 1H, H3 or H5), 5.45 (m, 2H, H5 & H6), 7.25 (m, 5H, aromatic H) ppm.

EXAMPLE 3

(3R,5S,6E,trans)-3,5-Dihydroxy-7-[3-methyl-5-oxo-1-(phenylmethyl)-2-pyrrolidinyl]-6-heptenoic acid, methylester 3-A. (3R,6E,trans)-3-[[(1,1-Dimethylethyl) dimethylsilyl]oxy]-5-oxo-7-[3-methyl-5-oxo-1-(phenylmethyl)-2-pyrrolidinyl]-6-heptenoic acid, methylester A solution of aldehyde compound 1-I (repurified by chromatography and characterized by $^1$H and $^{13}$C-NMR spectra prior to use) (137.5 mg, 0.633 mmol) and the chiral phosphonate compound 1-O (267 mg, 0.7 mmol) in dry acetonitrile (2.0 ml) was stirred under an atmosphere of dry nitrogen at ambient temperature and lithium chloride (29 mg, 0.7 mmol) and a solution 1, 8-diazabicyclo-[5,4,0]undec-7-ene (97 mg, 0.633 mmol) in dry acetonitrile (1.0 ml) was added. After 2.0 hours, the mixture was diluted with methylene chloride (30 ml), washed with a 5% potassium hydrogen sulfate solution (2×15 ml) and brine, dried (anhydrous magnesium sulfate) and evaporated to afford the crude product as an oil. This product was chromatographed on a column of Baker 60-200 silica gel, eluting the column with methylene chloride-hexane (1:1), methylene chloride and methylene chloride-ethyl acetate (9:1) to isolate compound 3-A as a homogeneous [thin layer chromatography ; $R_f$=0.86, silica gel, ethyl acetate; U.V. and iodine] oil (261 mg, 87.2%) with consistent $^1H$ and $^{13}C$-NMR spectral data. While the two diastereomers present in this sample could not be distinguished from the $^1H$-NMR spectrum (CDCl$_3$, FX-270), the $^{13}C$-NMR spectrum showed that two diastereomers (about 1:1) were present.

3-B.
(3R,6E,trans)-3-Hydroxy-5-oxo-7-(3-methyl-5-oxo-1-(phenylmethyl)-2-pyrrolidonyl]-6-heptenoic acid, methylester A solution of compound 3-A (261 mg, 0.552 mmol) in acetonitrile (3.0 ml) was stirred for 1½ hours with 48% aqueous hydrofluoric acid (0.2 ml) at ambient temperature. The mixture was then diluted with methylene chloride (25 ml), washed with brine, a dilute sodium hydrogen carbonate solution and brine, dried (anhydrous magnesium sulfate) and evaporated to afford the crude product as an oil. This oil was chromatographed on Baker 60-200 silica gel (15 g), eluting the column with methylene chloride-hexane (1:1), methylene chloride and methylene chloride-ethyl acetate (8:2) to isolate compound 3-B as a homogeneous (thin layer chromatography, silica gel, ethyl acetate) oil (163 mg, 82%) with consistent $^1H$ and $^{13}C$-NMR spectral data. It was a mixture (about 1:1) of two diastereomers on the basis of the $^{13}C$-NMR spectrum Characteristically, in the $^1H$-NMR spectrum the benzylic methylene and olefinic protons β- to the carbonyl group of the two diastereomers showed different chemical shifts.

3-C.
(3R,5S,6E,trans)-3,5-Dihydroxy-7-[3-methyl-5-oxo-1-(phenylmethyl)-2-pyrrolidinyl]-6-heptenoic acid, methylester A solution of compound 3-B (163 mg, 0.45 mmol) in dry tetrahydrofuran (1.5 ml) was stirred with pivalic acid (4 mg) and a 1.0M solution of triethylboron in tetrahydrofuran (0.7 ml) for 20 minutes under an atmosphere of dry nitrogen It was then cooled to −78° C. in a dry ice-acetone bath and sodium borohydride (23 mg, 0.60 mmol) was added, followed dropwise by dry methanol (0.6 ml). After 1.0 hour, a solution of 30% hydrogen peroxide (1.0 ml) in water (1.0 ml) was added cautiously, the mixture was warmed up to ambient temperature and was stirred for 30 minutes. It was then added into brine (25 ml) containing 1.0 N hydrochloric acid (2.0 ml) and extracted with ethyl acetate. The extracts were combined, washed with brine and a dilute sodium hydrogen carbonate solution and brine, dried (magnesium sulfate) and evaporated to afford the crude product as an oil. This product was chromatographed on a column of Baker 60-200 silica gel (10 g), eluting the column with methylene chloride, methylene chloride-ethyl acetate (1:1), ethyl acetate and ethyl acetate-methanol (95:5) to isolate homogeneous (thin layer chromatography; silica gel; ethyl acetate-methanol, 95:5) Example 3 as an oil (151 mg, 92.2%) with consistent $^1H$ and $^{13}C$-NMR spectral data. While the two diastereomers present (about 1:1) in this were not distinguishable from the $^{13}C$-NMR spectrum, the methyl and benzylic methylene groups showed different chemical shifts in the $^1H$-NMR spectrum (CDCl$_3$, FX-270) suggesting the presence of two diastereomers (about 1:1).

EXAMPLE 4

(3R,5S,6E,trans)-3,5-Dihydroxy-7-[3-methyl-5-oxo-1-(phenylmethyl)-2-pyrrolidinyl]-6-heptenoic acid, monolithium salt A solution of Example 3 (151 mg, 0.415 mmol) in tetrahydrofuran was stirred with 1.0N lithium hydroxide (0.45 ml) under an atmosphere of nitrogen at ambient temperature for 30 minutes. The mixture was then concentrated in vacuo, dissolved in distilled water (3.0 ml) and applied on a HP-20 polymer column (3"×1¼"). The column was eluted successively with deionized water (250 ml) and methanol-water (3:7; 200 ml). The methanol-water eluate was concentrated in vacuo and lyophilized to afford the homogeneous [thin layer chromatography, $R_f$=0.25; silica gel; ethyl acetate-hexane-acetic acid 8:2:1, U.V. and Ce-Mo-H$_2$SO$_4$-heat] analytical specimen of Example 4 as a colorless, fluffy solid (147 mg, 92.4%) with consistent IR and $^1H$-NMR spectral data.

Analysis calculated for $C_{19}H_{24}LiNO_5$/0.79 water (MW: 353.35/367.48): C, 62.10; H, 7.01: N, 3.81%. Found: C, 62.12; H, 6.89; N, 3.79%.

IR Spectrum (KBr): $\mu_{max}$3408–3440 Cm$^{-1}$ (strong, OH), 1664 Cm$^{-1}$ (strong, C=O, amide), 1588, 1421 Cm$^{-1}$ (strong, C=O, COO—).

$^1H$-NMR Spectrum (FX-270, DMSO-D$_6$): δ0.95 (2 doublets, 3H, J=~8.0, H$_{19}$), ~3.5 (H$_8$), 3.8, 4.7 (2 quartets, 1H each, H$_{12}$), 3.73 (1H, m, H$_3$ or H$_5$), 4.15 (1H, m, H$_3$ or H$_5$), 5.42 (2H, m, H$_5$ & H$_6$), ~7.25 (5H, m, aromatic H) ppm.

EXAMPLE 5

(3R,5S,cis)-3,5-Dihydroxy-7-[3-methyl-5-oxo-1-phenylmethyl)-2-pyrrolidinyl heptanoic acid, methylester 5-A.
(3R,cis)-3-[[(1,1-Dimethylethyl)dimethylsilyl[oxy]-5-oxo-7-[3-methyl-5-oxo-1-(phenylmethyl)-2-pyrrolidinyl]-6-heptanoic acid, methylester A solution of compound 1-P (450 mg) in ethyl acetate (10 ml) containing 10% palladium on charcoal (75 mg) was stirred under an atmosphere of hydrogen for 1.0 hour. The mixture was then filtered through a bed of Celite and evaporated to afford compound 5-A as an oil (440 mg, 9.95%) with consistent $^1H$ and $^{13}C$ NMR spectral data. It was homogeneous by thin layer chromatography (silica gel, ethyl acetate) and was more polar than compound 1-P.

5-B.
(3R,cis)-3-Hydroxy-5-oxo-7-[3-methyl-5-oxo-1-(phenylmethyl)-2-pyrrolidinyl]-6-heptanoic acid, methylester A solution of compound 5-A (440 mg, 0.93 mmol) in acetonitrile (12 ml) was stirred at ambient temperature with 48% hydrofluoric acid for 1.0 hour. The mixture was diluted with brine (50 ml) and extracted with ethyl acetate (3×20 ml). The extracts were combined, washed with a dilute sodium bicarbonate solution and brine, dried (anhydrous magnesium sulfate) and evaporated to afford an oil. This oil was purified on a column of silica gel (Baker 60-200 mesh, 15 g), eluting the column with methylene chloride and methylene chloride-ethyl acetate mixtures to afford homogeneous (thin layer chromatography; ethyl acetate, silica gel, $R_f=0.32$) compound 5-B as an oil (90 mg, 86.4%) with consistent $^1$H-NMR and $^{13}$C-NMR data.

5-C.

(3R,5S,cis)-3,5-Dihydroxy-7-[3-methyl-5-oxo-1-(phenylmethyl)-2-pyrrolidinyl]- heptanoic acid, methylester A solution of compound 5-B (290 mg, 0.80 mmol) in dry tetrahydrofuran (1.5 ml) containing 1.0M triethylborane in tetrahydrofuran (1.2 ml) and pivalic acid (5.0 mg) was stirred at ambient temperature under an atmosphere of nitrogen for 25 minutes. Then, the mixture was cooled to −78° C. in a dry ice-acetone bath and sodium borohydride (41 mg, 1.1 mmol) was added, followed dropwise by methanol (1.0 ml). After 1.0 hour, 30% hydrogen peroxide (1.05 ml) diluted with water (1.0 ml) was cautiously added, and the mixture was warmed up to room temperature and was stirred for 30 minutes. It was then acidified by the addition of 1.0 N hydrochloric acid (1.5 ml), diluted with brine (20 ml) and extracted with ethyl acetate (3×15 ml). The extracts were combined, washed with a dilute sodium bicarbonate solution and brine, dried (anhydrous magnesium sulfate) and evaporated to afford an oil. This oil was chromatographed on a column of silica gel (Baker 60-200 mesh, 12 g), eluting the column successively with methylene chloride, methylene chloride-ethyl acetate mixtures, ethyl acetate and ethyl acetate-methanol (9:1) to afford homogeneous (thin layer chromatography, silica gel; ethyl acetate-methanol 9:1; $R_f=0.4$) Example 5 as an oil (2.59 mg, 88.6%) with a consistent $^{13}$C-NMR spectrum.

EXAMPLE 6

(3R,5S,cis)-3,5-Dihydroxy-7-[3-methyl-5-oxo-1-(phenylmethyl)-2-pyrrolidinyl]heptanoic acid, monolithium salt A solution of compound 5-C (259 mg, 0.71 mmol) in tetrahydrofuran (3.0 ml) was stirred with 1.0 N lithium hydroxide (0.72 ml) at ambient temperature under an atmosphere of nitrogen for 1.0 hour. It was then concentrated in vacuo to remove the tetrahydrofuran, dissolved in distilled water and applied on a 1¼"×3" column bed of HP-20. The column was eluted first with deionized water (300 ml) and then with methanol-deionized water (3:7, 300 ml). The latter eluate was evaporated and lyophilized to afford Example 6 as small, heavy crystals (227 mg, 83%) containing 167 moles of water. It was homogeneous by thin layer chromatography (silica gel, ethyl acetate acetic acid-hexane, 8:2:1; $R_f=0.45$; visualization with a ceric sulfate-ammonium molybdate-sulfuric acid solution with heating).

IR Spectrum (KBr): ~3420 cm$^{-1}$ (Strong, OH), 1666, 1585 (cm$^{-1}$ (Strong, C=O), $^1$H-NMR Spectrum (DMSO-d$_6$, FX-270): δ0.91 (d, 3H, J = ~7.0, H$_2$L0), 3.51 (m, 1H, H$_5$), 3.75 (m, 1H, H$_3$), 4.03 (d, 1H, J=15.0, H$_{13}$), 7.25 (m, 5H, -, aromatic H) ppm.

EXAMPLE 7

(3R,5S,trans)-3,5-Dihydroxy-7-[3-methyl-5-oxo-1-(phenylmethyl)-2-pyrrolidinyl]heptanoic acid, methylester

7-A.

(3R,trans)-3-[[(1,1-Dimethylethyl)dimethylsilyl]oxy]-5-oxo-7-[3-methyl-5-oxo-1-(phenylmethyl)-2-pyrrolidinyl]-6-heptanoic acid, methylester A solution of the chiral diasteomeric mixture (1:1) of compound 3-A (450 mg, 0.95 mmol) in ethyl acetate (8 ml) was stirred with 10% palladium on charcoal (60 mg, Aldrich Chemical Company) under an atmosphere of hydrogen for 1.5 hours. A thin layer chromatography examination (silica gel, ethyl acetate) showed the presence of a single more polar product. The mixture was filtered through a bed of Celite, washing the Celite with ethyl acetate, and evaporated to afford compound 7-A as an oil (440 mg, 97.5%) with consistent H$^1$ and C$^{13}$ NMR spectral data.

7-B (3R,trans)-3-Hydroxy-5-oxo-7-[3-methyl-5-oxo-1-(phenylmethyl)-2-pyrrolidinyl]-6-heptanoic acid, methylester A solution of compound 7-A (440 mg, 0.93 mmol) in acetonitrile (6 ml) was stirred with 48% hydrofluoric acid (0.25 ml) at ambient temperature for 1.0 hour. The mixture was then diluted with brine (50 ml) and extracted with ethyl acetate (3×20 ml). The extracts were combined, washed with a dilute sodium bicarbonate solution and water, dried and evaporated to afford the crude product as an oil. This oil was chromatographed on a column of Baker 60-200 mesh silica gel (15 g) using dichloromethane and dichloromethane-ethyl acetate mixtures for elution to afford compound 7-B as a homogeneous (thin layer chromatography) oil (290 mg, 86%) with consistent H$^1$ and C$^{13}$ NMR spectral data.

7-C.

(3R,5S,trans)-3,5-Dihydroxy-7-[3-methyl-5-oxo-1-(phenylmethyl)-2-pyrrolidinyl]-heptanoic acid, methylester A solution of compound 7-B (290 mg, 0.8 mmol) in dry tetrahydrofuran (2.0 ml) was stirred for 20 minutes at ambient temperature with 1M triethylborane in tetrahydrofuran (1.3 ml) and pivalic acid 5.0 mg) under an atmosphere of nitrogen. The mixture was then cooled in a dry ice acetone bath at −78° C. Solid sodium borohydride (41 mg, 1.1 mmol) was added, followed dropwise by methanol (1.0 ml). After 1.0 hour, 30% hydrogen peroxide (1.05 ml) diluted with water (1.0 ml) was added cautiously. The mixture was warmed up to ambient temperature and was stirred for 30 minutes. It was then diluted with water (30 ml), 1.0N hydrochloric acid (2.0 ml) was added, and the mixture was extracted with ethyl acetate (3×20 ml). The extracts were combined, washed with a dilute sodium bicarbonate solution and brine, dried (magnesium sulfate anhydrous) and evaporated to afford the crude product as an oil. This product was chromatographed on a column of Baker 60-200 mesh silica gel (12 g) eluting the column successively with dichloromethane and ethyl acetate dichloromethane (8:2 and 1:1) to afford Example 7 as a homogeneous (thin layer chromatography; silica gel; ethyl acetate-methanol, 97:3; $R_f=0.32$) oil (292 mg, 100%) with consistent H$^1$ and C$^{13}$ NMR spectral data.

EXAMPLE 8

(3R,5S, trans)-3,5-Dihydroxy-7-[3-methyl-5-oxo-1-(phenylmethyl)-2-pyrrolidinyl]heptanoic acid, monolithium salt A solution of Example 7 (292 mg, 0.8 mmol) in tetrahydrofuran (2 ml) was stirred under an atmosphere of nitrogen with 1.0N lithium hydroxide (0.8 ml) for 40 minutes. The mixture was then poured on an HP-20 polymer column bed (3"×1¼") which was eluted successively with 4 column volumes of deionized water and 8 column volumes of methanol-deionized water (3:7). The second eluate was evaporated in vacuo and lyophilized to afford a hydrated form of Example 8 as a white solid (252 mg, 85.8%). It was homogeneous by thin layer chromatography (silica gel; ethyl acetate-hexane-acetic acid, 8:2:1; $R_f=0.27$) and showed elemental analysis, IR and $H^1$ NMR data consistent with the structure.

Elemental analysis calculated for $C_{19}H_{26}NOLi/0.75\ H_2O$ (MW=355.36/13.5): C,61.87; H,7.51; N,3.80; Found: C,61.84; H,7.54; N,3.78.

IR spectrum (KBr): $\mu_{max}$ 3383 to 3421 $Cm^{-1}$ (strong,OH); 1583, 1664 $Cm^{-1}$ (strong, C=O).

$H^1$NMR spectrum (DMSO-$d_6$): δ0.93 (d, 3H, J=@7.0, $H_{19}$), 2.47, 2.55 (m, 2H, $H_2$), 2.88 (m, 1H, $H_8$), 3.50, 3.75 (m, 1H each, $H_3$ and $H_5$), 3.88, 3.95 (d,@0.5 H each, J=@16.0, $H_{12}$), 4.73, 4.8 (d,@0.5H each, J=@16.0, $H_{12}$) and 7.25 (m,4H,aromatic H) ppm.

EXAMPLE 9

(3R,5S,6E,trans)-7-[3-(4-Fluorophenyl)-1-(1-methylethyl)-5-oxo-2-pyrrolidinyl]-3,5-dihydroxy-6-heptenoic acid, methylester

9-A. trans-4-Fluoro cinnamic acid, ethyl ester

Sodium hydride (60% dispersion in mineral oil, 2 g, 50 mmol) was washed twice with dry hexane, suspended in dry tetrahydrofuran (30 ml), stirred and cooled down to 0° C. (ice bath) under an atmosphere of nitrogen. To this suspension was added slowly a solution of triethylphosphonoacetate (11.21 g, 50 mmol) in dry tetrahydrofuran (30 ml) and the mixture was then warmed up to room temperature. After 1 hour, the solution was recooled to 0° C. (ice bath). A solution of p-fluorobenzaldehyde (5.83 g, 47 mmol) in dry tetrahydrofuran (10 ml) was slowly added and the mixture was warmed up to room temperature. After another 1.0 hour, the mixture was quenched with 5 drops of acetic acid, diluted with 50 ml of brine, concentrated in vacuo and extracted with ethyl acetate (3×50 ml). The ethyl acetate extracts were combined, washed with brine, dried over anhydrous magnesium sulfate and evaporated in vacuo to leave a syrup. This syrup was chromatographed on a column of silica gel (150 g, Baker 60-200 mesh) eluting with ethyl acetate-hexane (1:4) to give 8.2 g (89%) of thin layer chromatography-homogeneous compound 9-A as an oil with consistent $^1$H-NMR and $^{13}$C-NMR spectra.

9-B.

5,5-Diethoxycarbonyl-4-(4-fluorophenyl)-2-pyrrolidinone

To a solution of sodium (125 mg), 5.43 mmol) in absolute ethanol (40 ml) was added, diethyl acetamidomalonate (6.08 g, 28 mmol) at room temperature under an atmosphere of nitrogen. Compound 9-A (7.76 g, 40 mmol) was then slowly added. The mixture was refluxed for 18 hours, cooled to room temperature and neutralized with acetic acid. Ethanol was evaporated in vacuo. The residue was diluted with brine and extracted with ethyl acetate (120 ml). The ethyl acetate extract was dried over anhydrous magnesium sulfate and evaporated in vacuo. The residue was crystallized from ethyl ether-hexane (3:1) to give 6.5 g (50.3%) of thin layer chromatography-homogeneous compound 9-B as a solid with consistent $^1$H-NMR and $^{13}$C-NMR spectra. Compound 9-B may also be prepared by the procedures described in A. B. Mauger, J. Org. Chem. 46, 103 (1981); G. H. Cocolas and W. H. Hartung, J. Amer. Chem. Soc., 79, 5203; and W. H. Hartwig and L. Born, J. Org. Chem., 52, 4352 (1987).

9-C.

5,5-Diethoxycarbonyl-N-(1-methylethyl)-4-(4-fluorophenyl)-2-pyrrolidinone

A solution of compound 9-B (3.23 g, 10 mmol) in dry dimethylformamide (15 ml) was added to a suspension of sodium hydride (60% dispersion in mineral oil, 580 mg, 14.5 mmol) in dry dimethylformamide (10 ml) at room temperature under an atmosphere of nitrogen. The mixture was stirred for 20 minutes for the evolution of gas to cease and a solution of 2-iodopropane (3.4 g, 20 mmol) in dry dimethylformamide was added. The mixture was then stirred for 18 hours. The resulting solution was poured slowly into brine (80 ml) and extracted with ethyl ether (2×80 ml). The combined extracts were washed with water, dried over anhydrous magnesium sulfate and evaporated in vacuo. The residue was chromatographed on a column of silica gel (100 g, Baker 60-200 mesh), eluting the ethyl acetate-hexane (1:9) to give 2.9 g (79.4%) of compound 9-C as an oil with consistent $^1$H-NMR and $^{13}$C-NMR spectra.

9-D.

trans-5-Ethoxycarbonyl-1-methylethyl-4-(4-fluorophenyl)-2-pyrrolidinone and

9-E.

cis-5-Ethoxycarbonyl-(1-methylethyl)-4-(4-fluorophenyl)-2-pyrrolidinone

To a solution of compound 9-C (2.83 g, 7.74 mmol) in 30 ml of 95% ethanol under an atmosphere of nitrogen was added dropwise 8.13 ml of 1 N sodium hydroxide solution. After the addition was complete, the mixture was stirred at room temperature for 5.5 hours and then acidified with 5% hydrochloric acid to a pH of 2. The ethanol was evaporated in vacuo. The residue was diluted with brine and extracted with ethyl acetate (3×60 ml). The combined ethyl acetate extracts were dried over anhydrous magnesium sulfate and evaporated in vacuo to give a foam. This foam was heated in an oil bath (preheated to 160°) for 5 minutes, until the evolution of gas ceased, to give 2 g of a gummy residue. Another run on the same scale gave 2 g more of gummy material. These were combined (4.0 g) and flash-chromatographed on a column of silica gel (LPS-1, 200 g), eluting with ethyl acetate-hexane (1:4 and 3:7) to give in order of increasing polarity compound 9-D (trans isomer, 1.5 g white solid, 32.3%) and compound 9-E (cis isomer, 1.75 g white solid, 37.9%) with consistent $^1$H-NMR and $^{13}$C-NMR spectra.

9-F.
trans-5-[[1-(1-Methylethyl)-4-(fluorophenyl)]-2-oxo-pyrrolidonyl]carboxaldehyde To a chilled (ice bath) and stirred suspension of lithium borohydride (1 g, 45.91 mmol) in dry tetrahydrofuran (15 ml) under an atmosphere of nitrogen was added dropwise a solution of compound 9-D (1.5 g, 5.11 mmol). The mixture was gradually warmed up to room temperature and dry methanol (1.3 g, 40.5 mmol) was added dropwise. After 18 hours, the resulting mixture was slowly poured into 5% hydrochloric acid and stirred for 30 minutes. The tetrahydrofuran and methanol were removed in vacuo. The residue was diluted with brine (50 ml) and extracted with ethyl acetate (3×75 ml). The combined ethyl acetate extracts were washed with a saturated column bicarbonate solution, dried over anhydrous magnesium sulfate and evaporated in vacuo to give a gummy residue. This residue was chromatographed on a column of silica gel (50 g, Baker 60-200 mesh) eluting with ethyl acetate-hexane (1:1) to give 1.1 g of thin layer chromatography-homogeneous compound 9-F, (1.1 g, 87.0%) as a white solid with consistent $^1$H-NMR and $^{13}$C-NMR spectra.

9-G.
trans-5-[[1-(1-Methylethyl)-4-(4-fluorophenyl)]-2-oxo-pyrrolidinyl]-methanol To a stirred suspension of Dess-Martin periodinane (371 mg, 0.875 mmol) in dry dichloromethane (4 ml) under an atmosphere of nitrogen was added dropwise a solution of compound 9-F (200 mg, 0.796 mmol) in dry dichloromethane (2 ml) and t-butanol (83 μl, 0.88 mmol). The mixture was stirred for 1.0 hour at room temperature and poured into a mixture of sodium bicarbonate (535 mg, 6.36 mmol) and 0.5 M solution thiosulfate (8 ml) in dichloromethane (10 ml). The mixture was stirred until the organic and aqueous layers were both clear. The organic layer was separated, washed with brine, dried over anhydrous magnesium sulfate and evaporated in vacuo to give compound 9-G (190 mg, 95.8%) as a gum with consistent $^1$H-NMR and $^{13}$C-NMR spectra The two (chiral) diastereomers which were present (about 1:1) on the basis of NMR spectral data were not readily separable by chromatography.

Another run with 400 mg of compound 9-F gave 390 mg more of compound 9-G.

9-H.
(3R,6E,trans)-3-[[(1,4-Dimethylethyl)dimethylsilyl]oxy]-5-oxo-7-[1-(dimethyl)methyl-5-oxo-4-(4-fluorophenyl)-2-pyrrolidinyl]-6-heptenoic acid, methylester To a mixture of compound 9-G (190 mg, 0.762 mmol), the chiral β-keto phosphonate compound 1-0 (335 mg, 0.876 mmol) and lithium chloride (42 g, 0.99 mmol) in 3 ml of dry acetonitrile was added a solution of 1,8-diazabicyclo[5,4,0]-undec-7-ene (116 mg, 0.762 mmol) in 1.0 ml of dry acetonitrile at room temperature under an atmosphere of nitrogen. After 2.5 hours, the mixture was diluted with dichloromethane (50 ml), washed with 5% potassium bisulfate solution and brine, dried over anhydrous magnesium sulfate and evaporated in vacuo. The residue was flash-chromatographed on a column of silica gel (LPS-1, 100 g) eluting with ethyl acetate-dichloromethane to give 282 mg (73.2%) of thin layer chromatography-homogeneous compound 9-H as a oil with consistent $^1$H-NMR and $^{13}$C-NMR spectra.

Another run with 390 mg of compound 9-G gave 590 mg more of compound 9-H. The two (chiral) diastereomers which were present (about 1:1) on the basis of NMR spectral data were not readily separable by chromatography.

9-I.
(3R,6E,trans)-3-Hydroxy-5-oxo-7-[1-(dimethyl)methyl-5-oxo-4-(4-fluorophenyl)-2-pyrrolidinyl]-6-heptenoic acid, methylester To a chilled (0°, ice bath) and stirred solution of compound 9-H (600 mg, 1.19 mmol) in 12 ml of acetonitrile under an atmosphere of nitrogen was added 48% hydrofluoric acid (1.0 ml). After 1.0 hour, water (1 ml) and sodium bicarbonate (1 g) was added. The mixture was warmed up to room temperature and stirred about 10 minutes. The combined ethyl acetate extracts were washed with brine, dried over anhydrous magnesium sulfate and evaporated in vacuo. The residue was chromatographed on a column of silica gel (Baker 60-200 mesh, 70 g) eluting with ethyl acetate-dichloromethane (1:4 and 1:1) to give 400 mg (86.1%) of thin layer chromatography-homogeneous compound 9-I as a gum with consistent $^1$H-NMR and $^{13}$C-NMR spectra. Two (chiral) diastereomers were present (about 1:1) on the basis of NMR spectral data.

9-J.
(3R,5S,6E,trans)-7-[3-(4-Fluorophenyl)-1-(1-methylethyl)-5-oxo-2-pyrrolidinyl]-3,5-dihydroxy-6-heptenoic acid, methylester A solution of compound 9-I (400 mg, 1.02 mmol), triethylborane (1.0 M solution in tetrahydrofuran, 1.53 ml, 1.53 mmol) and pivalic acid (7 mg) in 4 ml of dry tetrahydrofuran was stirred at room temperature under an atmosphere of nitrogen for 25 minutes and then cooled to −78° C. (dry ice-acetone bath). Sodiumborohydride (48.3 mg, 1.28 mmol) was then added, followed dropwise by methanol (2.5 ml). After 1.5 hours of stirring −78° C., a solution of hydrogen peroxide (30%) in 2 ml of water was added. The mixture was gradually warmed to room temperature, stirred for 30 minutes and concentrated in vacuo. The residual slurry was acidified with 5% hydrochloric acid to a pH of 4, saturated with sodium chloride and extracted with ethyl acetate (3×25 ml). The combined ethyl acetate extracts were washed with brine, dried over anhydrous magnesium sulfate and evaporated in vacuo. The residue was chromatographed on a column of silica gel (Baker 60-200 mesh, 50 g), eluting with ethyl acetate-dichloromethane (1:1) to give 270 mg (67.3%) of thin layer chromatography-homogeneous Example 9 as a gum with consistent $^1$H-NMR and $^{13}$C-NMR spectra. Two (chiral) diastereomers which were present (about 1:1) on the basis of NMR spectral data.

EXAMPLE 10
(3R,5S,6E,trans)-7-[3-(4-Fluorophenyl)-1-(1-methylethyl)-5-oxo-2-pyrrolidinyl]-3,5-dihydroxy-6-heptenoic acid, monolithium salt A solution of Example 9 (125 mg, 0.318 mmol) and lithium hydroxide (1.0 N solution, 0.32 ml, 0.32 mmol) in 3 ml of tetrahydrofuran was stirred at room temperature under an atmosphere of nitrogen for 1.0 hour and concentrated in vacuo. The residue was dissolved in water (about 2.0 ml) chromatographed on a column of HP-20 (1"×3.5" bed), eluting with water (about 250 ml)

and methanol-water (1:1, 250 ml). The latter eluates were combined, evaporated in vacuo to dryness and lyophilized overnight to give 93 mg (75.9%) of the analytical specimen of Example 10 (a mixture of 2 chiral diastereomers, ~1:1) as a solid with consistent Mass, IR and $^1$H-NMR spectral data.

Analysis calculated for $C_{20}H_{25}FNO_5Li \cdot H_2O$: C,59.56; H,6.75; N,3.47; F,4.71. Found: C,59.80; H,6.59; N,3.33; F,4.74.

IR Spectrum (KBr): $\mu_{max}$3408 cm$^{-1}$ (OH), 1663 cm$^{-1}$ (amide C=O), 1587 cm$^{-1}$ (Salt C=O).

Mass Spectrum: $(M+H)^+ = 386$, $(M-H)^- = 384$, $(M-Li)^- = 378$.

$^1$H-NMR Spectrum of Example 10 (GX270, DMSO-d$_6$) δ1.17 (m,6H,H$_{13}$+H$_{14}$), 1.25 (m,1H,H$_{4a}$), 1.45 (m,1H,H$_{4b}$), 1.80 (m,1H,H$_{2a}$), 2.00 (m,1H,H$_{2b}$), 2.35 (m,1H,H$_{10a}$), 2.69 (m,1H,H$_{10b}$), 3 13 (m,1H,H$_9$), 3.69 (m,1H,H$_8$), 3.95 (m,1H,H$_{12}$), ~3.95 (m,1H,H$_5$), 4.12 (m,1H,H$_3$), 5.53 (m,1H,H$_6$H$_7$), 7.14 and 7.32 (m,4H,H$_{16}$+H$_{17}$+H$_{19}$+H$_{20}$)ppm.

EXAMPLE 11

(3R,5S,trans)-7-[3-(4-Fluorophenyl)-1-(1-methylethyl)-5-oxo-2-pyrrolidinyl]-3,5-dihydroxyheptanoic acid, methylester A mixture of Example 9 (140 mg, 0.356 mmol), a mixture of 2 chiral diastereomers, Ca.1:1) and 10% palladium on carbon (15 mg) in 20 ml of ethyl acetate was hydrogenated at room temperature under atmospheric pressure for 2 hours. The resulting solution was filtered through a bed of HYFLO® and washed with a small amount of ethyl acetate. The filtrate and washing were evaporated in vacuo to give a gum. This gum was chromatographed on a column of silica gel (20 g, Baker 60-200 mesh) eluting with ethyl acetate-dichloromethane (1:1) and ethyl acetate to give 135 mg (95.9%) of the thin layer chromatography-homogeneous compound 11-A as a gum with consistent $^1$H-NMR and $^{13}$C-NMR spectra.

EXAMPLE 12

(3R,5S,trans)-3-(4-Fluorophenyl)-3,5-dihydroxy-1-(1-methylethyl)-5-oxo-2-pyrrolidineheptanoic acid, monolithium salt A solution of Example 11 (125 mg, 0.318 mmol) and 1 N lithium hydroxide (0.35 ml, 0.35 mmol) in 3 ml of tetrahydrofuran was stirred at room temperature under an atmosphere of nitrogen for 1.0 hour. The solvent was mostly evaporated in vacuo. The residue was dissolved in some water and chromatographed on a HP-20 column, eluting with deionized water and water-methanol (1:1) to give thin layer chromatography-homogeneous Example 12 as a foam. This foam was lyophilized overnight to give 79 mg (64.5%) of Example 12 hydrate as a colorless solid (a mixture of 2 chiral diasteromers) with consistent analytical, IR, Mass and $^1$H-NMR spectral data. Analysis calculated for $C_{20}H_{27}FNO_5Li \cdot 0.82$ H$_2$O (MW=387.38+0.83 H$_2$O): Calculated: C,59.70; H,7.18; N,3.48; F,4.72. Found: C,59.62; H,7.22; N,3.56; F,4.76.

IR Spectrum (KBr): $\mu_{max}$3413 cm$^{-1}$ (—OH, H$_2$O), 1662 cm$^{-1}$ (C=O, amide), 1585 cm$^{-1}$ (C=O, salt)

Mass: $(M+H)^+ = 3.82$, $(M+H+Li)^+ = 388$, $(M+H)^- = 380$, $(M-H+Li)^- = 386$ (free acid)

$^1$H-NMR Spectrum of Example 12 (DMSO-d$_6$, GX270): δ1.18 (d,1H,J= ~8.0, H$_{13}$ or H$_{14}$), 1.20 (d,1H,J= ~8.0,H$_{14}$ or H$_{13}$), 1.84 (m,1H H$_{2a}$), 2.06 (m,2H,H$_{2b}$+H$_{10a}$), 2.86 (m,1H,H$_{10b}$), 3.19 (m,1H,H$_9$), 3.45 (m,1H,H$_8$), 3.60 (m,1H,H$_{12}$), 3.77 (m,1H,H$_3$ or H$_5$), 3.87 (m,1H,H$_5$ or H$_3$), 7.18 (m,4H,H$_{16}$+H$_{17}$+H$_{19}$+H$_{20}$)ppm.

EXAMPLE 13

(3R,5S,6E,Cis)-7-3-(4-Fluorophenyl)-1-(1-methylethyl)-5-oxo-2-pyrrolidinyl]-3,5-dihydroxy-6-heptenoic acid, methylester

13-A.

cis-5-[[1-Dimethylmethyl-4-(4-fluorophenyl)]-2-oxopyrrolidinyl]-methanol

To a chilled (0°, ice bath) and stirred suspension of lithium borohydride (1.0 g, 45.91 mmol) under an atmosphere of nitrogen was added dropwise a solution of compound 9-E (1.5 g, 5.11 mmol) in 15 ml of dry tetrahydrofuran. The mixture was then warmed up to room temperature and methanol (1.3 g, 40.57 mmol) was added. After 3 days, the resulting mixture was slowly poured into 5% hydrochloric acid and stirred for 30 minutes. The organic solvent was evaporated in vacuo. The slurry was diluted with brine (30 ml) and extracted with ethyl acetate (3×50 ml). The combined ethyl acetate extracts were washed with a saturated sodium hydrogen carbonate solution and brine, dried over anhydrous magnesium sulfate and evaporated in vacuo to give a gum. This gum was chromatographed on a column of silica gel (55 g, Baker 60-200 mesh), eluting with ethyl acetate-dichloromethane (1:4) to give 1.2 g (81.4%) of thin layer chromatography-homogeneous compound 13-A as a solid with consistent $^1$H-NMR and $^{13}$C-NMR spectra.

13-B.

cis-5-[[1-Dimethylmethyl-4-(4-fluorophenyl)]-2-oxopyrrolidinyl]-carboxaldehyde To a stirred suspension of Dess-Martin periodinane (317 mg, 0.875 mmol) in 4 ml of dry dichloromethane at room temperature under an atmosphere of nitrogen was added dropwise a solution of compound 13-A (200 mg, 0.796 mmol) in 2 ml of dry dichloromethane and dry t-butyl alcohol (83 µl, 0.88 mmol). After 1 hour, the mixture was poured slowly into a stirred mixture of sodium bicarbonate (535 mg) and 0.5 M sodium thiosulfate (8 ml) in 20 ml of dichloromethane. The mixture was stirred vigorously, until the dichloromethane and water layers were clear, the dichlormethane layer was separated, washed with brine, dried over anhydrous magnesium sulfate and evaporated in vacuo to give 190 mg (95.5%) of compound 13-B as a white solid with consistent $^1$H-NMR and $^{13}$C-NMR spectrum. This solid was used in the next step without purification.

Another run with 400 mg of compound 13-A gave 390 mg more of compound 13-B.

13-C.

(3R,6E,cis)-3-[[(1,1-Dimethylethyl)dimethylsilyl]oxy]-5-oxo-7-[3[1-(dimethyl)methyl]-5-oxo-4-(4-fluorophenyl)]-2-pyrrolidinyl]-6-heptenoic acid, methylester To a stirred mixture of compound 13-B (190 mg, 0.762 mmol), the β-keto phosphonate ester compound 1-O (335 mg, 0.876 mmol) and lithium chloride (42 mg, 0.99 mmol) in 3 ml of dry acetonitrile at room temperature under an atmosphere of nitrogen was added dropwise a solution of 1,8-diazabicycle[5,4,0]undec-7-ene (116 mg, 0.762 mmol) in 1.0 ml of dry acetonitrile. After 2.5 hours, the resulting mixture was diluted with dichloromethane (50 ml), washed with a 5% potassium hydrogen sulfate solution and brine, dried over anhydrous magnesium sulfate and evaporated in vacuo to give an oil. This oil was flash-chromatographed on a column of silica gel (50 g, LPS-1), eluting with ethyl acetate-dichloromethane (1:9) to give 282 mg (61.0%) of thin layer chromatography-homogeneous compound 13-C as an oil with consistent $^1$H-NMR and $^{13}$C-NMR spectra.

Another run with 390 mg of compound 13-B gave 480 mg more of compound 13-C.

13-D.
(3R,6E,cis)-3-Hydroxy-5-oxo-7-[1-(dimethyl)methyl-5-oxo-4-(4-fluorophenyl)-2-pyrrolidinyl]-6-heptenoic acid, methylester To a chilled (0° C., ice bath) and stirred solution of compound 13-C (500 mg, 0.989 mmol) in 10 ml of acetonitrile under an atmosphere of nitrogen was added dropwise 48% hydrofluoric acid (1.6 ml). After 75 minutes, water (1 ml) and sodium bicarbonate (500 mg) were added carefully. The resulting mixture was warmed up to room temperature, stirred for 20 minutes, diluted with brine and extracted with ethyl acetate (3×30 ml). The combined ethyl acetate extracts were washed with brine, dried over anhydrous magnesium sulfate and evaporated in vacuo to give a gum. This product was chromatographed on a column of silica gel (60 g, Baker 60-200 mesh) eluting with ethyl acetate-chloromethane (1:4 and 1:1) to give 400 mg (86.1%) of thin layer chromatography-homogeneous compound 13-D as a thick oil with consistent $^1$H-NMR and $^{13}$C-NMR spectra.

13-E.
(3R,5S,6E,cis)-7-[3-(4-Fluorophenyl)-1-(dimethylmethyl)-5-oxo-2-pyrrolidinyl]-3,5-dihydroxy-6-heptenoic acid, methylester A mixture of compound 13-D (400 mg, 1.02 mmol), triethylborane (1 M solution in tetrahydrofuran, 1.53 ml, 1.53 mmol) and pivalic acid (7 mg) in 3.5 ml of dry tetrahydrofuran was stirred at room temperature under an atmosphere of nitrogen for 25 minutes and then cooled to −78° C. (dry ice-acetone bath). Sodium borohydride (48.3 mg, 1.28 mmol) and methanol (2 ml) were then successively added. After 1.5 hours at −78° C. a solution of 30% hydrogen peroxide (3.5 ml) in 2 ml of water was added dropwise. The mixture was gradually warmed up to room temperature and stirred for 30 minutes. The organic solvent was evaporated in vacuo. The residual slurry was acidified with 5% hydrochloric acid to pH=3, saturated with sodium chloride and extracted with ethyl acetate (3×25 ml). The combined ethyl acetate extracts were washed with brine, dried over anhydrous magnesium sulfate and evaporated in vacuo to give a gum. This gum was chromatographed on a column of silica gel (40 g, Baker 60-200 mesh), eluting with ethyl acetate-dichloromethane (1:1), ethyl acetate and dichloromethane-methanol (95:5) to give 240 mg (72.4%) of the thin layer chromatography-homogeneous Example 13 as a thick oil with consistent $^1$H-NMR and $^{13}$C-NMR spectra.

EXAMPLE 14
(3R,5R,6E,cis)-7-[3-(4-Fluorophenyl)-1-(1-methylethyl)-5-oxo-2-pyrrolidinyl]-3,5-dihydroxy-6-heptenoic acid, monolithium salt A mixture of Example 13 (110 mg, 0.28 mmol) and 1 N lithium hydroxide (0.3 ml, 0.3 mmol) in 3 ml of tetrahydrofuran was stirred at room temperature under an atmosphere of nitrogen for 1 hour. The solvent was evaporated in vacuo to dryness. The residue was chromatographed on a column of HP-20 eluting with water (about 250 ml) and water-methanol (1:1 mixture, about 250 ml) to give the thin layer chromatography-homogeneous Example 14 as a foamy solid. This foamy solid was lyophilized overnight to give 78 mg (72.3%) of Example 14 hydrate as a colorless solid with consistent analytical, IR, Mass and $^1$H-NMR spectral data.

Analysis calculated for $C_{20}H_{25}NFO_5Li \cdot 0.62 H_2O$ (MW = 396.53 + 0.62 $H_2O$): Calculated: C,60.57; H,6.67; N,3.53; F,4.79. Found: C,60.59; H,6.70; N,3.51; F,5.06.

IR Spectrum (KBr): $\mu_{max}$3422 cm$^{-1}$ (OH,$H_2O$), 1663 cm$^{-1}$ (C=O, amide), 1589 cm$^{-1}$ (C=O, salt).

Mass spectrum: $(M+H)^+ = 380$ $(M+H+Li)^+ = 386$ (Salt). $(M-H)^- = 378$, $(M-H+Li)^- = 384$ (acid).

$^1$H-NMR spectrum of Example 14 (DMSO-d$_6$, GX270): δ0.99 (m,1H$_{4a}$), 1.08 (d,3H,J=~8.0,H$_{13}$ or H$_{14}$), 1.20 ((d,3H,J=~8.0,H$_{14}$or H$_{13}$), 1.25 (m,1H,H$_{4b}$), 1.70 (m,1H, H$_{2a}$), 1.92 (m,1H,H$_{2b}$), 2.40 (dd,1H,H$_{10a}$), 2.77 (dd,1H,H$_{10b}$), 3.50 (m,1H,H$_9$), 3.70 (m,1H,H$_8$), 3.96 (m,2H,H$_{12}$+H$_5$), 4.38 (dd,1H,H$_3$), 5.16 (m,1H,H$_7$), 5.42 (m,1H,H$_6$), 7.10 and 7.22 (m,m,4H,H$_{16}$+H$_{17}$+H$_{19}$+H$_{20}$) ppm.

EXAMPLE 15
(3R,5R,cis)-7-[3-(4-Fluorophenyl)-1-(1-methylethyl)-5-oxo-2-pyrrolidinyl]-3,5-dihydroxyheptanoic acid, methylester A solution of Example 13 (130 mg, 0.33 mmol), a mixture of 2 chiral diastereomers, about 1:1) containing a suspension of 10% palladium on carbon (13 mg) in 15 ml of ethyl acetate was hydrogenated under atmosphere pressure under stirring at room temperature for 2 hours. The mixture was filtered through a bed of HYFLO to remove the catalyst. The filtrate was evaporated in vacuo to give a thick oil. This oil was chromatographed on a column of silica gel (20 g, Baker 60-200 mesh) eluting with ethyl acetate-(dichloromethane (1:1 mixtures) and ethyl acetate to give 115 mg (88%) of thin layer chromatography-homogeneous Example 15 with consistent $^1$H-NMR and $^{13}$C-NMR spectra.

EXAMPLE 16
(3R,5S,cis)-3-(4-Fluorophenyl)-3,5-dihydroxy-1-(1-methylethyl)-5-oxo-2-pyrrolidineheptanoic acid, monolithium salt A mixture of Example 15 (110 mg, 0.278 mmol) and 1 N lithium hydroxide (305 μl, 0.305 mmol) in 3 ml of tetrahydrofuran was stirred at room temperature under an atmosphere of nitrogen for 1 hour. The solvent was mostly evaporated in vacuo. The concentrate was dissolved in some water and was chromatographed on a 1"×3½" column bed of HP-20, eluting successively with deionized water (about 250 ml) and methanol-water (3:7, about 250 ml) to give thin layer chromatography-homogeneous Example 16 as a foamy solid. This was lyophilized overnight to give 65 mg (60.4%) of Example 16 hydrate as a colorless solid with consistent analytical, IR, Mass, and $^1$H-NMR spectra data.

Analysis for $C_{20}H_{27}FLiNO_5 \cdot 0.97 H_2O$ (MW=404.86 H$_2$O): Calculated: C,59.34; H,7.20; N,3.46; F,4.69. Found: C,59.39; H,7.17; N,3.41; F,4.78.

IR Spectrum (KBr): $\mu_{max}$3412 cm$^{-1}$ (OH,H$_2$O), 1664 cm$^{-1}$ (C=O, amide), 1587 cm$^{-1}$ (C=O, salt).

Mass spectrum: (M+H)+=382, (M+H+Li)+=388 (for acid), (M-H)-=380, (M-H+Li)-=386 (for acid).

$^1$H-NMR spectrum of Example 16 (DMSO-d$_6$, GX270): δ0.88 (m,2H,H$_4$), 1.23 (d,3H,J=~8.0,H$_{13}$ or H$_{14}$), 1.29 (d,3H,J=~8.0,H$_{14}$ or H$_{13}$), 1.72 (m,1H,H$_{2a}$), 1.93 (m,1H,H$_{2b}$), 2.32 (dd,1H,H$_{10a}$), 2.72 (m,1H,H$_{10b}$), 3.65 (m,2H,H$_8$+H$_9$), 3.90 (m,2H,H$_5$+H$_{12}$), 4.41 (m,1H,H$_3$), 7.15 and 7.36 (m,4H,H$_{16}$+H$_{17}$+H$_{19}$H$_{20}$)ppm.

The spectrum showed two doublets for the C$_{13}$ or C$_{14}$ methyl groups indicating that the compound was a mixture of two diastereomers (Ca. 1:1).

EXAMPLE 17

(3R,5S,6E,cis)-7-[1-[4-Fluorophenyl)methyl]-3-(1-methylethyl)-5-oxo-2-pyrrolidinyl]-3,5-dihydroxy-6-heptenoic acid, methylester

7-A. E-4,4-Dimethyl-2-butenoic acid, ethyl ester

Sodium hydride (60% dispersion in mineral oil, 2 g, 50 mmol) was washed twice with dry hexane, dried in vacuo for 1.0 hour, suspended in dry tetrahydrofuran (30 ml) and cooled in an ice bath under an atmosphere of nitrogen. A solution of triethyl-phosphonoacetate (11.21 g, 50 mmol) in dry tetrahydrofuran (30 ml) was added dropwise. After the addition was complete, the solution was warmed up to room temperature, stirred for 1.0 hour and recooled in the ice bath. A solution of isobutyraldehyde (3.39 g, 47 mmol) in dry tetrahydrofuran (10 ml) was then added. The mixture was gradually warmed up to room temperature and stirred for 5.0 hours. A few drops of acetic acid were added. The reaction mixture was diluted with brine (50 ml). The tetrahydrofuran was removed in vacuo. The residual slurry was extracted with ethyl acetate (3×70 ml). Ether is preferred for extraction. The ethyl acetate extracts were combined, washed with brine, dried over anhydrous magnesium sulfate and evaporated in vacuo at room temperature to give an oil. This oil was chromatographed on a column of silica gel (100 g, Baker 60-200 mesh), eluting with ethyl acetate-hexane (5:95) to give 4.05 g (60.6%) of the thin layer chromatography-homogeneous compound 17-A as an oil with consistent $^1$H-NMR and $^{13}$C-NMR spectra. Ether-hexane mixture is recommended for chromatography. An attempted distillation at 15 mm (bath temperature, about 100°) in the presence of hydroquinone caused extensive dimerization.

17-B.
5,5-Diethoxycarbonyl-4-(1-methyl)ethyl-2-pyrrolidinone

To a stirred solution of sodium (100 mg) in absolute dry ethanol (40 ml) was added diethyl acetamidomalonate (4.07 g, 18.75 mmol) at room temperature under an atmosphere of nitrogen. After 10 minutes, compound 17-A (4 g, 28.13 mmol) was slowly added. After the addition was complete, the mixture was heated under reflux for 20 hours. The mixture was then allowed to come to room temperature and neutralized with acetic acid. The ethanol was evaporated in vacuo. The residual slurry was diluted with brine and extracted with ethyl acetate (120 ml). The ethyl acetate extract was washed with water, dried over anhydrous magnesium sulfate and evaporated in vacuo to give a solid. This solid was recrystallized from ethyl ether-hexane to give 3.5 g (45.9%) of thin layer chromatography-homogeneous compound 17-B as a colorless solid, melting point 95°-96° C., with consistent $^1$H-NMR and $^{13}$C-NMR spectra. See, for example, A. B. Mauger, J. Org. Chem.; 46, 1032 (1981) and W. Hartwig and L. Born, J. Org. Chem., 52, 4352 (1987).

7-C.
5,5-Diethoxycarbonyl-1-[(4-fluorophenyl)methyl]-4-(1-methylethyl)-2-pyrrolidinone Sodium hydride (60% dispersion in mineral oil, 568 mg, 14.19 mmol) was washed twice with dry hexane, dried in vacuo for 30 minutes and suspended in dry dimethylformamide (15 ml). A solution of compound 17-B (3.5 g, 12.9 mmol) in dry dimethylformamide (10 ml) was added dropwise at room temperature under an atmosphere of nitrogen. After 1.0 hour, the solution was cooled to 0° (ice bath) and a solution of 4-fluorobenzyl bromide (2.92 g, 15.48 mmol) in dry dimethylformamide (5.0 ml) was added dropwise for 5 minutes. The solution was gradually warmed up to room temperature, stirred for 1.5 hours, poured into brine (70 ml) and extracted with ethyl ether (3×60 ml). The combined ethyl ether extracts were washed with water (2×60 ml), dried over anhydrous magnesium sulfate and evaporated in vacuo to give an oil. This oil was chromatographed on a column of silica gel (120 g, Baker 60-200 mesh) eluting with ethyl acetate-hexane (5:95 and 1:9) to give 4.1 g (83.8%) of thin layer chromatography-homogeneous compound 17-C as an oil with consistent $^1$H-NMR and $^{13}$C-NMR spectra.

17-D.
cis-5-Ethoxycarbonyl-1-[(4-fluorophenyl)methyl]-4-(1-methyl)-ethyl-2-pyrrolidinone and

17-E.
trans-5-Ethoxycarbonyl-1-[(4-fluorophenyl)methyl]-4-(1-methyl)-ethyl-2-pyrrolidinone A stirred solution of compound 17-C (4.0 g, 10.54 mmol) in 95% ethanol (40 ml) at room temperature under an atmosphere of nitrogen was treated with 1.0 N sodium hydroxide (11.07 ml, 11.07 mmol). After 5 hours, the resulting solution was acidified with 5% hydrochloric acid to a pH of 2. The ethanol was then evaporated in vacuo to give a slurry. This slurry was diluted with brine (70 ml) and extracted with ethyl acetate (4×50 ml). The combined ethyl acetate extracts were washed with brine, dried over anhydrous magnesium sulfate and evaporated in vacuo to give a solid. This solid was then heated at 170° (preheated oil bath temperature) until the evolution of gas ceased (about 10 minutes). The gummy residue was allowed to cool and was flash-chromatographed on a column of silica gel (200 g, LPS-1), eluting with ethyl acetate-hexane (15:85 and 25:75) to give, in order of increasing polarity, compound 17-D (1.6 g, 49.4%, cis isomer) and compound 17-E (340 mg, 10.5%, trans isomer) with consistent $^1$H-NMR and $^{13}$C-NMR spectra.

17-F.
cis-[[(4-Fluorophenyl)-methyl]-4-(1-methylethyl)-2-oxo-pyrrolidinyl]-5-methanol To a chilled (0°, ice bath) and stirred suspension of lithium borohydride (870 mg, 39.94 mmol) in dry tetrahydrofuran (5 ml) under an atmosphere of nitrogen was added dropwise a solution of compound 17-D 91.3 g, 423 mmol) in 15 ml of tetrahydrofuran. After the addition was temperature and methanol (1.13 g, 35.27 mmol) was added dropwise. After 18 hours, the resulting solution was poured slowly into 5% hydrochloric acid, stirred for 30 minutes and extracted with ethyl acetate (3×75 ml). The combined ethyl acetate extracts were washed with a saturated sodium bicarbonate solution and brine, dried over anhydrous magnesium sulfate and evaporated in vacuo to give a gum. This gum was chromatographed on a column of silica gel (50 g, Baker 60-200 mesh), eluting with ethyl acetate-dichloromethane (1:4 and 1:1) to give 0.9 g (80.2%) of the thin layer chromatography-homogeneous compound 17-F as a solid, melting point 133°134° C., with consistent $^1$H-NMR and $^{13}$C-NMR spectra.

17-G.
cis-[[(4-Fluorophenyl)-methyl-4-(1-methylethyl)-2-oxopyrrolidinyl]-5-carboxaldehyde To a stirred suspension of Dess-Martin periodinane (371 mg, 0.875 mmol) in dichloromethane (4 ml) at room temperature under an atmosphere of nitrogen was added a solution of compound 17-F (200 mg, 0.796 mmol) in dichloromethane (2 l) followed by t-butyl alcohol (83 μl, 0.88 mmol). After 1.0 hour, the mixture was poured into a stirred solution of sodium bicarbonate (506 mg, 6.03 mmol) in 0.5M sodium thiosulfate (7.54 ml, 3.77 mmol) and dichloromethane (20 ml). The mixture was stirred vigorously until the two layers were clear. The dichloromethane layer was separated, washed with brine, dried over anhydrous magnesium sulfate and evaporated in vacuo to give 190 mg (98.2%) of thin layer chromatography-homogeneous compound 17-G as an oil, with consistent $^1$H-NMR and $^{13}$C-NMR spectra. This oil was used in the next step without further purification. Another run using 400 mg (1.508 mmol) of compound 17-F gave 396 mg more of compound 17-G.

17-H.
(3R,6E,cis)-3-[[(1,1-Dimethylethyl)dimethylsilyl]oxy]-7-[1-[[(4-fluorophenyl)methyl]-3-(1-methylethyl)-5-oxo-2-pyrrolidinyl]-3-hydroxy-5-oxo-6-heptenoic acid, methylester To a stirred mixture of compound 17-G (190 mg, 0.721 mmol), the chiral β-ketophosphonate ester compound 1-O (317 mg, 0.83 mmol) and lithium chloride (40 mg, 0.938 mmol) in dry acetonitrile (3.0 ml) at room temperature under an atmosphere of nitrogen was added dropwise a solution of 1,8-diazabicyclo-[5,4,0]undec-7-ene (108 μl, 0.721 mmol) in dry acetonitrile (1.0 ml). After 2.5 hours, the reaction mixture was diluted with dichloromethane (50 ml), washed with a 5% potassium hydrogen sulfate solution and brine, dried over anhydrous magnesium sulfate and evaporated in vacuo to give an oil. This oil was chromatographed on a column of silica gel (50 g, Lps-1) eluting with ethyl acetate-dichloromethane (1:9) to give 250 mg (66.7%) of thin layer chromatography-homogeneous compound 17-H as an oil with consistent $^1$H-NMR and $^{13}$C-NMR spectra. Another run using 390 mg (1.48 mmol) of compound 17-G gave 520 mg more of compound 17-H. This compound and subsequent compounds in this preparation are all mixtures of two chiral diastereomers (about 1:1) since the phosphonate compound 1-O was chiral.

17-I.
(3R,6E,cis)-3-Hydroxy-7-[1-[(4-fluorophenyl)methyl]-3-(1-methylethyl)-5-oxo-2-pyrrolidinyl]-5-oxo-6-heptenoic acid, methylester A chilled (ice bath) and stirred solution of compound 17-H (750 mg, 1.44 mmol) in acetonitrile (12 ml) under an atmosphere of nitrogen was treated with 48% hydrofluoric acid (2.0 ml). After 1.0 hour, water (1 ml) and solid sodium bicarbonate (2.0 g) were added. The mixture was warmed up to room temperature, stirred for 20 minutes, diluted with brine (30 ml) and extracted with ethyl acetate (3×30 ml). The combined ethyl acetate extracts were washed with brine, dried over anhydrous magnesium sulfate and evaporated in vacuo to give a gum. This gum was chromatographed on a column of silica gel (60 g, Baker 60–200 mesh) eluting with ethyl acetate-dichloromethane (1:4 and 1:1) to give 510 mg (87.2%) of thin layer chromatography-homogeneous compound 17-I as a gum with consistent $^1$H-NMR and $^{13}$C-NMR spectra.

17-J.
(3R,5S,6E,cis)-7-[1-[(4-Fluorophenyl)methyl]-3-(1-methylethyl)-5-oxo-[2-pyrrolidinyl]-3,5-dihydroxy-6-heptenoic acid, methylester A mixture of compound 17-I (500 mg, 1.23 mmol), triethylborane (1.0M solution in tetrahydrofuran, 1.85 ml, 1.85 mmol) and pivalic acid (9 mg) in dry tetrahydrofuran (4.0 ml) was stirred for 30 minutes at room temperature under an atmosphere of nitrogen and then cooled to −78° (dry-ice acetone bath). Sodium borohydride (58 mg, 1.54 mmol was then added, followed dropwise by dry methanol (2 ml). After 1.5 hours, a solution of 30% hydrogen peroxide (2.0 ml) in water (2.0 ml) was cautiously added (gas evolution). The mixture was then warmed up to room temperature (gas evolution), stirred for 30 minutes and acidified with 10% hydrochloric acid to a pH of 2. After 1.0 hour, the organic solvent was evaporated in vacuo. The residual slurry was saturated with sodium chloride and extracted with ethyl acetate (3×25 ml). The combined ethyl acetate extracts were washed with brine, dried over anhydrous magnesium sulfate and evaporated in vacuo to give a gum. This gum was chromatographed on a column of silica gel (50 g, Baker 60–200 mesh), eluting successively with ethyl acetate-dichloromethane (1:1) and ethyl acetate to give 350 mg (69.7%) of thin layer chromatography (TLC) homogeneous Example 17 as a gum with consistent $^1$H-NMR and $^{13}$C-NMR spectra.

EXAMPLE 18
(3R,5S,6E,cis)-7-[1-[(4-Fluorophenyl)methyl]-3-(1-methylethyl)-5-oxo-2-pyrrolidinyl]-3,5-dihydroxy-6-heptenoic acid, monolithium salt A stirred solution of Example 17 (125 mg, 0.307 mmol) in tetrahydrofuran (3.0 ml) was treated with 1.0N lithium hydroxide (337 μl, 0.337 mmol) at room temperature under an atmosphere of nitrogen. After 1.0 hour, the solvent was evaporated in vacuo. The gummy residue was chromatographed on a column of HP-20

(1.0" s 1.0" column bed) eluting successively with water and methanol-water (3:7) to give in the latter eluate thin layer chromatography-homogeneous Example 18. This eluate was evaporated in vacuo and lyophilized overnight to give 80 mg (65.3%) of a hydrated analytical specimen of Example 18 as a white solid with consistent, IR, Mass, and $^1$H-NMR spectral data.

Analysis for $C_{21}H_{27}FNO_5Li.0.25H_2O$: Calc'd.: C, 62.46; H, 6.86; N, 3.47; F, 4.70, Found: C, 62.20; H, 7.17; N, 3.54; F, 4.77.

IR Spectrum (KBr): $\mu_{max}$ 3394 cm$^{-1}$ (—OH), 1669 cm$^{-1}$ (C=O, amide) 1584 cm$^{-1}$ (C=O, acid salt).

Mass: $(M+H)^+ = 400$, $(M+H)^+ + Li = 406$, $(M+H) + 2Li = 412$. $(M-H)^- = 392$, $(M-H)^- + Li = 398$.

$^1$H NMR spectrum of Example 18 (DMSO-$d_6$, GX270) δ 0.80 (m,6H,$H_{13}+H_{13}$), 1.34 (m,1H,$H_{12}$), 1.45 (m,2H,$H_9+H_{10a}$), 1.94 (m,3H,$H_4+H_{10b}$), 2.21 (q,2H,$H_2$), 3.72 (m,3H,$H_5+H_8+H_{15a}$), 4.16 (m,1H,$H_3$), 4.72 (d,1H,J=~20,$H_{15b}$), 5.50 (m,2H,$H_6+H_7$), 7.18 (m,4H,$H_{17}+H_{18}+H_{20}+H_{21}$) ppm.

EXAMPLE 19

(3R,5S,6E,trans)-7-[1-[(4-Fluorophenyl)methyl]-3(1-methylethyl)-5-oxo-[2-pyrrolidinyl]-3,5-dihydroxy-6-heptenoic acid, methylester

19-A.

trans-[[(4-Fluorophenyl)methyl]-4-(1-methyl)ethyl-2-oxo-pyrrolidinyl]-5-methanol To a chilled (0° C., ice bath) and stirred suspension of lithium borohydride (200 mg, 9.18 mmol) in dry tetrahydrofuran (4 mL) under an atmosphere of nitrogen was added dropwise a solution of Compound 17-E (300 mg, 0.976 mmol) in dry tetrahydrofuran (3 mL). After the addition was complete, the mixture was warmed up to room temperature and methanol (260 mg, 8.11 mmol) was added dropwise. After 18 hours, the resulting solution was poured slowly into 5% hydrochloric acid, stirred for 30 minutes and extracted with ethyl acetate (3×20 mL). The combined ethyl acetate extracts were washed with a saturated sodium bicarbonate solution and brine, dried over anhydrous magnesium sulfate and evaporated in vacuo to give a gum. This gum was chromatographed on a column of silica gel (50 g, LPS-1) eluting with ethyl acetate-dichloromethane (1:4 and 1:1) to give 210 mg (81.1%) of the TLC-homogeneous Compound 19-A as a solid, m.p. 92°-93°, with consistent $^1$-NMR and $^{13}$C-NMR spectra.

19-B.

trans-[[(4-Fluorophenyl)-methyl]-4-(1-methyl)ethyl-2-oxo-pyrrolidinyl]-5-carboxaldehyde To a stirred suspension of Dess-Martin periodinane (352 mg, 0.829 mmol) in dichloromethane (4 mL) at room temperature under an atmosphere of nitrogen was added dropwise a solution of Compound 19-A (200 mg, 0.754 mmol) in dichloromethane (2 mL) followed by t-butyl alcohol (78 μL, 0.829 mmol). After 1.0 hour, the resulting mixture was poured into a stirred solution of sodium bicarbonate (506 mg) in 0.5M solution thiosulfate (7.5 mL) and dichloromethane (20 mL). The mixture was stirred vigorously until the two layers were clear. The dichloromethane layer was separated, washed with brine, dried over anhydrous magnesium sulfate and evaporated in vacuo to give 185 mg (93.2%) of slightly impure (TLC) Compound 19-B as a gum. This gum was used in the next step without further purification.

19-C.

(3R,6E,trans)-3-[[1,1-Dimethylethyl)dimethylsilyl]oxy]-7-[1-[(4-fluorophenyl)methyl]-3-(1-methylethyl)-5-oxo-2-pyrrolidinyl]-3-hydroxy-5-oxo-6-heptenoic acid, methylester To a stirred mixture of Compound 19-B (185 mg, 0.702 mmol), the chiral β-ketophosphonate ester compound 1O (309 mg, 0.806 mmol) and lithium chloride (39 mg, 0.913 mmol) in dry acetonitrile (3 mL) at room temperature under an atmosphere of nitrogen was added dropwise a solution of 1,8-diazabicyclo[5,4,0]undec-7-ene (105 μL, 0.702 mmol) in dry acetonitrile (1 mL). After 2.5 hours, the reaction mixture was diluted with dichloromethane (50 mL), washed with a 5% potassium hydrogen sulfate solution and brine, dried over anhydrous magnesium sulfate, and evaporated in vacuo to give an oil. This oil was chromatographed on a column of silica gel (50 g, Lps-1) eluting with ethyl acetate-dichloromethane (1:9) to give 300 mg (68.5%) of the TLC-homogeneous Compound 19-C as an oil with consistent $^1$H-NMR and $^{13}$C-NMR spectra. This product and subsequent compounds in this preparation are all mixtures of two chiral diastereomers (about 1:1) since the phosphonate compound 1-O was chiral.

19-D.

(3R,6E,trans)-3-Hydroxy-7-[1-[(4-fluorophenyl)methyl]-3-(1-methylethyl)-5-oxo-2-pyrrolidinyl]-5-oxo-6-heptenoic acid, methylester A chilled (ice bath) and stirred solution of Compound 19-C (300 mg, 0.577 mmol) in acetonitrile (6 ml) under an atmosphere of nitrogen was treated with 48% hydrofluoric acid (1 ml). After 1.5 hours, water (1 ml) and sodium bicarbonate (1 g) were added. The mixture was warmed up to room temperature, stirred for 30 minutes, diluted with brine (915 ml) and extracted with ethyl acetate (3×20 ml). The combined ethyl acetate extracts were washed with brine, dried over anhydrous magnesium sulfate and evaporated in vacuo to give a gum. This gum was chromatographed on a column of silica gel (25 g, Baker 60-200 mesh), eluting with ethyl acetate-dichloromethane (1:4 and 1:1) to give 220 mg (94.0%) of TLC-homogeneous Compound 19-D (a mixture of two chiral diastereomers) with consistent $^1$H-NMR and $^{13}$C-NMR spectra.

19-E.

(3R,5S,6E,trans)-7-[1-[(4-Fluorophenyl)methyl]-3-(1-methylethyl)-5-oxo-[2-pyrrolidinyl]-3,5-dihydroxy-6-heptenoic acid, methylester A mixture of Compound 19-D (220 mg, 0.543 mmol), triethylborane (1.0M solution in tetrahydrofuran, 814 μl, 0.814 mmol) and pivalic acid (4 mg) in dry tetrahydrofuran (2 ml) was stirred for 30 minutes at room temperature under an atmosphere of nitrogen and then cooled to −78° C. (dry-ice-acetone bath). Sodium borohydride (25.7 mg, 0.678 mmol) was then added, followed dropwise by dry methanol (1.0 ml). After 1.5 hours, a solution of 30% hydrogen peroxide (2 ml) in water (2 ml) was cautiously added (gas evolution). The mixture was then warmed up to room temperature, stirred for 30 minutes and acidified with 5% hydrochloric acid to a pH of 2. After 1.0 hour, the organic solvent was evaporated in vacuo. The residual slurry was saturated with sodium chloride and extracted with ethyl acetate (3×20 ml). The combined ethyl acetate extracts were washed with brine, dried over anhydrous magnesium sulfate and evaporated in vacuo to give a gum. This gum was chromatographed on a column of silica gel (20 g, Baker 60–200 mesh) eluting successively with ethyl acetate-dichloromethane (1:1) and ethyl acetate to give 200 mg (90.5%) of Example 19 (a mixture of 2 chiral diastereomers) as a TLC-homogeneous gum with consistent $^1$H-NMR and $^{13}$C-NMR spectra.

EXAMPLE 20

(3R,5S,6E,trans)-7-[1-[(4-Fluorophenyl)methyl]-3-(1-methylethyl)-5-oxo-2-pyrrolidinyl]-3,5-dihydroxy-6-heptenoic acid, monolithium salt A stirred solution of Example 19 (100 mg, 0.245 mmol) in tetrahydrofuran (3 ml) was treated with 1.0N lithium hydroxide (267 µl, 0.267 mmol) at room temperature under an atmosphere of nitrogen. After 1.0 hour, the solvent was evaporated in vacuo. The gummy residue was chromatographed on an HP-20 column (1 inch length, 1 inch diameter bed) eluting successively with water (250 ml) and 30% methanol-water (250 ml) to give in the latter eluate TLC-homogeneous Example 20. The later eluate was evaporated in vacuo and lyophilized overnight to give 68 mg (69.4%) of a hydrated analytical specimen of Example 20 as a white solid with consistent IR, Mass, and $^1$H-NMR spectral data.

Anal. for $C_{21}H_{27}FNO_5Li \cdot 0.25H_2O$: Calc'd: C, 62.46; H, 6.86; N, 3.47; F, 4.70; Found: C, 62.72; H, 7.16; N, 3.49; F, 4.55.

IR Spectrum (KBr): $\mu_{max}$ 3392 cm$^{-1}$ (OH), 1663 cm$^{-1}$ (C=O, amide), 1584 cm$^{-1}$ (C=O, acid salt).

Mass: $(M+H)^+ = 400$, $(M+H)^+ + Li = 406$, $(M-H)^- = 392$, $(M-H)^- + Li = 398$.

$^1$H-NMR Spectrum of Example 20 (DMSO-d$_6$, GX270) δ 0.77 (m, 6H, H$_{13}$+H$_{14}$), 1.31 (m, 1H, H$_{12}$), 1.55 (m, 2H, H$_4$), 1.87 (m, 2H, H$_2$), 2.05 (m, 2H, H$_9$+H$_{10a}$), 2.42 (dd, 1H, H$_{10b}$), 3.55 (m, 1H, H$_8$), 3.72 (m, 1H, H$_5$), 3.82 and 3.88 (two d, each about ½H, H$_{15a}$), 4.14 (m, 1H, H$_3$), 4.66 (d, 1H, H$_{15b}$), 5.37 and 5.57 (two m, 1H each, H$_6$+H$_7$), 7.16 (m, 4H, H$_{17}$+H$_{18}$+H$_{20}$+H$_{21}$) ppm.

The $^1$H-NMR Spectrum (DMSO-d$_6$, 270 MHz) showed 5 peaks centered at δ 0.77 for the methyls of the isopropyl group, and 2 doublets centered at δ 3.82 and 3.88 and 1 doublet centered at δ4.66 for the methylenes of the benzyl group indicating that Example 20 was a mixture of two diastereomers, as expected.

EXAMPLE 21

(3R,5R,trans)-7-[1-[(4-Fluorophenyl)methyl]-3-(1-methylethyl)-5-oxo-[2-pyrrolidinyl]-3,5-dihydroxy-6-heptenoic acid, methylester A mixture of Example 19 (100 mg, 0.245 mmol, a mixture of two chiral diastereomers) and 10% palladium on carbon (10 mg) in ethyl acetate (4 mL) was hydrogenated at room temperature under atmospheric pressure for 6 hours. The resulting solution was filtered through a bed of HYFLO and washed with a small amount of ethyl acetate. The filtrate was evaporated in vacuo to give slightly impure (TLC) Example 21 as a gum. This gum was chromatographed on a column of silica gel (15 g, Baker 60–200 mesh) eluting successively with ethyl acetate-dichloromethane (1:1) and ethyl acetate to give 95 mg (94.5%) of TLC-homogeneous Example 21 (a mixture of two chiral diastereomers) as a gum with consistent $^1$H-NMR and $^{13}$C-NMR spectra.

EXAMPLE 22

(3R,5S,trans)-1-[(4-Fluorophenyl)methyl]-3,5-dihydroxy-3-(1-methylethyl)-5-oxo-2-pyrrolidineheptanoic acid, monolithium salt A stirred solution of Example 21 (95 mg, 0.232 mmol) in tetrahydrofuran (2 mL) was treated with 1.0N lithium hydroxide (255 µL, 0.255 mmol) at room temperature under an atmosphere of nitrogen. After 1.0 hour, the solvent was evaporated in vacuo to give a gum. This gum was dissolved in water and chromatographed on an HP-20 column (1.5"×1.0" column bed), eluting successively with water (250 mL) and 30% methanol-water (250 mL) to give in the latter eluate TLC-homogeneous Example 22. This eluate was evaporated in vacuo and lyophilized to give 65 mg (69.8%) of the hydrated analytical specimen of Example 21 as a white solid with consistent IR, Mass and $^1$H-NMR spectral data. The 270 MHz $^1$H-NMR spectrum (DMSO-d$_6$) showed 6 peaks centered at δ 0.69 for the methyl groups of the isopropyl group, 2 doublets centered at 3.91 and 3.97 and 2 doublets centered at 4.68 and 4.73 for the methylenes of the benzyl group indicating that it was a mixture of 2 chiral diastereomers, as expected.

Anal. for $C_{21}H_{27}FNO_5Li \cdot 0.43H_2O$: Calc'd: C, 61.66; H, 7.36; N, 3.42; F, 4.64; Found: C, 61.70; H, 7.53; N, 3.38; F, 4.67.

IR Spectrum (KBr): $\mu_{max}$ 3414 cm$^{-1}$ (OH), 1662 cm$^{-1}$ (C=O, amide), 1583 cm$^{-1}$ (C=O, acid Salt).

Mass: $(M+H)^+ = 402$, $(M+H)^+ + Li = 408$, $(M-H)^- = 394$, $(M-H)^- + Li = 400$.

$^1$H-NMR Spectrum of Example 22 (DMSO-d$_6$, GX270): δ 0.69 (m, 6H, H$_{13}$+H$_{14}$), 1.38 (broad m, 7H, H$_4$+H$_6$+H$_7$+H$_{12}$), 1.84 (m, 2H, H$_2$), 2.03 (m, 2H, H$_9$+H$_{10a}$), 2.48 (m, 1H, H$_{10b}$), 3.11 (m, 1H, H$_8$), 3.56 (m, 1H, H$_5$), 3.78 (m, 1H, H$_3$), 3.91 and 3.97 (two d, ~½H each, J = ~17.0, H$_{15a}$), 4.68 and 4.73 (two d, ~½H each, J = ~17.0, H$_{15b}$), 4.70 (broad, 1H, OH), 7.16 and 7.28 (m each, 4H, H$_{17}$+H$_{18}$+H$_{20}$+H$_{21}$) ppm.

EXAMPLE 23

(3R,5R,cis)-3,5-Dihydroxy-1-[(4-fluorophenyl)methyl]-3-(1-methylethyl)-5-oxo-2-pyrrolidine heptanoic acid, methylester A solution of Example 17 (150 mg, 0.368 mmol, a mixture of two chiral diastereomers) containing a suspension of 10% palladium on carbon (15 mg) in ethyl acetate (5 mL) was hydrogenated under atmospheric pressure at room temperature for hours, and the mixture was filtered through a bed of HYFLO to remove the catalyst. The filtrate was evaporated in vacuo to give slightly impure (TLC) Example 23 as an oil. This oil was chromatographed on a column of silica gel (20 g, Baker 60–200 mesh) eluting successively with ethyl acetate-dichloromethane (1:1) and ethyl acetate to give 125 mg (82.9%) of Example 23 (a mixture of two chiral diastereomers) as a gum with consistent $^1$H-NMR and $^{13}$C-NMR spectra.

EXAMPLE 24

(3R,5R,cis)-3,5-Dihydroxy-1-[(4-fluorophenyl)methyl]-3-(1-methylethyl)-5-oxo-2-pyrrolidineheptanoic acid, monolithium salt A stirred solution of Example 23 (125 mg, 0.305 mmol, a mixture of two chiral diastereomers) in tetrahydrofuran (3 mL) at room temperature under an atmosphere of nitrogen was treated with 1.0N lithium hydroxide (336 μL, 0.336 mmol). After 1.0 hour, the solvent was evaporated in vacuo. The gummy residue was dissolved in water and chromatographed on a column of HP-20 (1.5"×1.0" column bed), eluting successively with water and 30% methanol-water to give in the later eluate TLC-homogeneous Example 24. This eluate was evaporated in vacuo and lyophilized overnight to give 85 mg (69.4%) of a hydrated analytical specimen of Example 24 as a white solid with consistent IR, Mass and $H^1$-NMR spectral data.

Anal. calc'd for $C_{21}H_{29}FNO_5Li\cdot 0.3H_2O$: C, 62.00; H, 7.33; N, 3.44; F, 4.67; Found: C, 62.12; H, 7.70; N, 3.39; F, 4.76.

IR Spectrum (KBr): $\mu_{max}$ 3396 cm$^{-1}$ (OH), 1666 cm$^{-1}$ (C=O, amide), 1585 cm$^{-1}$ (C=O, acid Salt.

Mass: $(M+H)^+ = 402$, $(M+Li)^+ = 408$, $(M-H)^- = 400$, $(M-Li)^- = 394$.

$H^1$-NMR Spectrum of Example 24 (DMSO-d$_6$, GX270): δ 0.85 (m, 6H, H$_{13}$+H$_{14}$), 1.00 to 2.3 (m, 12H, H$_2$+H$_4$+H$_6$+H$_7$+H$_9$+H$_{10}$+H$_{12}$), 3.46 (m, 2H, H$_5$+H$_8$), 3.75 (m, 1H, H$_3$), 3.92 and 3.98 (two d, each ~½H, H$_{15a}$) 4.70 (broad, 1H, OH) 4.76 and 4.79 (two d, each is ~½H, H$_{15b}$) 7.14 and 7.28 (m, 4H, H$_{17}$+H$_{18}$+H$_{20}$+H$_{21}$) ppm.

EXAMPLE 25

(3R*,5S*,cis)-7-[1-[(4-Fluorophenyl)methyl]-3-(1-methylethyl)-5-oxo-pyrrolidinyl]-3,5-dihydroxy-6-heptynoic acid, methylester

25-A.

1-[(4-Fluorophenyl)methyl]-3-(1-methylethyl)-5-oxo-pyrrolidinyl-2-ethyene

To a chilled (−40°, acetonitrile-dry ice bath) and stirred suspension of potassium tert-butoxide (64 mg, 0.57 mmol) in dry tetrahydrofuran (2 ml) under an atmosphere of nitrogen was added dropwise a solution of diethyl diazomethylphosphonate (012 mg, 0.57 mmol) in dry tetrahydrofuran (1.0 ml). (Diethyl diazomethylphosphonate was prepared by the composite procedure of D. Seyferth et al., *J. Org. Chem*, 36, 1384 (1971) and S. K. Davidson, G. W. Phillips and S. F. Martin et al., *Org. Synth.*, 65, p. 119 (1987).) After 1.0 hour, a solution of compound 17-G (100 mg, 0.38 mmol) in tetrahydrofuran (1.0 ml) was added dropwise. After 3.0 hours, 10% potassium hydrogen sulfate solution (3 ml) was added. The mixture was warmed up to room temperature, stirred for 20 minutes, diluted with brine (10 ml) and extracted with dichloromethane (3×10 ml). The combined dichloromethane extracts were washed with a 10% potassium hydrogen sulfate solution and brine, dried over anhydrous magnesium sulfate and evaporated in vacuo to give an oil. This oil was chromatographed on a column of silica gel (10 g, Baker 60–200 mesh), eluting with ethyl acetatehexane (2:8) to give 75 mg (76.2%) of TLC-homogeneous compound 25-A as a gum with consistent H$^1$-NMR and C$^{13}$-NMR spectra. Another run using 670 mg of compound 17-G gave 480 mg more of compound 25-A.

25-B.

1-[(4-Fluorophenyl)methyl]-3-(1-methylethyl)-5-oxo-pyrrolidinyl-2-3-(propynol)

To a chilled (−78°, Dry ice-acetone bath) and stirred solution of compound 25-A (380 mg, 1.46 mmol) in dry tetrahydrofuran (5 ml) under an atmosphere of nitrogen was added dropwise n-butyllithium (2.5M solution in hexane, 645 μL, 1.61 mmol). After 45 minutes, dry paraformaldehyde (220 mg, 7.33 mmol) was added. The mixture was stirred for 2 hours at −78°, 2 hours at 0° and 18 hours at room temperature. Brine (20 ml) was added and the resulting slurry was extracted with ethyl acetate (3×20 ml). The ethyl acetate extracts were washed with water, dried over anhydrous magnesium sulfate and evaporated in vacuo to give an oil. This was chromatographed on a column of silica gel (25 g, Baker 60–200 mesh) eluting successively with ethyl acetatehexane mixtures homogeneous compound 25-A as an oil with consistent H$^1$-NMR and C$^{13}$-NMR spectra. Another run using 292 mg of compound 13-A gave 143 mg more of compound 13-B. Unchanged compound 13-A also was isolated from both runs.

25-C.

1-[(4-Fluorophenyl)methyl]-3-(1-methylethyl)-5-oxo-pyrrolidinyl-2-3-(propynal)

To a stirred suspension of Dess-Martin periodinane (194 mg, 0.458 mmol) in dichloromethane (2 ml) at room temperature under an atmosphere of nitrogen was added dropwise a solution of compound 25-B (120 mg, 0.416 mmol) in dichloromethane (1.0 ml) followed by t-butyl alcohol (43 ml, 0.458 mmol). After 1.0 hour, the mixture was poured into a stirred mixture of sodium bicarbonate (280 mg, 3.33 mmol) in 0.5M sodium thiosulfate (4.2 ml, 2.1 mmol) and dichloromethane (15 ml). The mixture was stirred vigorously until the two layers were clear. The dichloromethane layer was separated, washed with brine, dried over anhydrous magnesium sulfate and evaporated in vacuo to give 119 mg (100%) of compound 25-C as a homogeneous (TLC) oil with consistent H$^1$-NMR and C$^{13}$-NMR spectra. Another run using 300 mg of compound 25-B gave 290 mg more of compound 25-C. These were used in the next step without purification.

25-D.

(5-R,S,cis)-7-[1-[(4-Fluorophenyl)methyl]-3-(1-methylethyl)-5-oxo-2-pyrrolidinyl]-5-hydroxy-3-oxo-6-heptynoic acid, methylester Sodium hydride (60% dispersion in mineral oil, 25 mg, 0.629 mmol) was washed twice with dry hexane, dried in vacuo for 30 minutes, suspended in dry tetrahydrofuran (1.5 ml), cooled in an ice bath and stirred under an atmosphere of nitrogen. A solution of methyl acetoacetate (73 mg, 0.629 mmol) in dry tetrahydrofuran (1 ml) was added dropwise and followed, after 30 minutes, dropwise by n-butyllithium (2.5M solution in hexane, 251 μl, 0.629 mmol). After another 30 minutes, the solution was cooled to −40° (dry ice-acetonitrile bath) and a solution of compound 25-C (120 mg, 0.419 mmol) in dry tetrahydrofuran (1.0 ml) was added dropwise. After 3 hours, the resulting solution was quenched with 60 mg of acetic acid, warmed up to room temperature, diluted with brine (10 ml) and extracted with ethyl acetate (3×15 ml). The combined ethyl acetate extracts were washed with a saturated sodium bicarbonate solution and brine, dried over anhydrous magnesium sulfate and evaporated in vacuo to give an oil. This oil was chromatographed on a column of silica gel (10 g, Baker 60–200 mesh) eluting successively with ethyl acetatehexane (4:6 and 1:1) to give 70 mg (41.4%) of TLC-homogeneous compound 25-D as an oil with consistent H$^1$-NMR and C$^{13}$-NMR spectra. Another run using 300 mg of compound 25-C gave 250 mg more of compound 25-D.

25-E. (3R*,5S*,cis)-7-[1-[(4-Fluorophenyl)methyl]-3-(1-methylethyl)-5-oxo-2-pyrrolidinyl]-3,5-dihydroxy-6-heptynoic acid, methylester A mixture of compound 25-D (300 mg, 0.744 mmol), triethylborane (1.0M solution in tetrahydrofuran, 1.12 ml, 1.12 mmol) and pivalic acid (6 mg) in dry tetrahydrofuran (3 ml) was stirred for 30 minutes at room temperature under an atmosphere of nitrogen and then cooled to −78° (Dry ice-acetone bath). Sodium borohydride (35.2 mg, 0.931 mmol) was added followed dropwise by dry methanol (2 ml). After 2 hours, a solution of 30% hydrogen peroxide (3 ml) in water (2 ml) was added dropwise. The mixture was then warmed up to room temperature, stirred for 1.0 hour and acidified with 5% hydrochloric acid to a pH of 3. (Use of longer reaction times, such as 2 to 3 hours, with more 30% hydrogen peroxide may improve the yield of the product.) After another hour, the organic solvent was evaporated in vacuo. The residual slurry was diluted with brine (15 ml) and extracted with ethyl acetate (4×15 ml). The combined ethyl acetate extracts were washed with brine, dried over anhydrous magnesium sulfate and evaporated in vacuo to give a gum. This gum was chromatographed on a column of silica gel (20 g, Baker 60–200 mesh), eluting successively with ethyl acetate-dichloromethane (1:4 and 1:1) to give 115 mg (38.1%) of TLC-homogeneous Example 25 as a gum with consistent $H^1$-NMR and $C^{13}$-NMR spectra. The $H^1$-NMR spectrum (CDCl$_3$, GX400) in the presence of a chiral europium shift reagent indicated that the compound was a mixture of two racemic diastereomers in nearly equal amounts.

EXAMPLE 26
(3R*,5S*,cis)-7-[1-[(4-Fluorophenyl)methyl]-3-(1-methylethyl)]3,5-dihydroxy-6-heptynoic acid, monolithium salt A stirred solution of Example 25 (90 mg, 0.223 mmol) in tetrahydrofuran (2 ml) at room temperature under an atmosphere of nitrogen was treated with 1.0N lithium hydroxide (244 µl, 0.244 mmol). After 1.0 hour, the solvent was evaporated in vacuo to give a gum. This gum was dissolved in water (2 ml) and chromatographed on a column of HP-20 (1"×1" column bed), eluting with deionized, distilled water (250 ml) and 30% methanol-deionized distilled water (250 ml) to give in the latter eluate TLC-homogeneous Example 26. This latter eluate was evaporated in vacuo and lyophilized overnight to give 65 mg (73.7%) of a hydrated analytical specimen of Example 26 as a white solid with consistent IR, mass and H-NMR spectral data. The presence of 6 singlets centered at δ 0.86 for the isopropyl methyl protons in the 270 MHz spectrum in DMSO-d$_6$ was indicative of the presence of 2 racemic diastereomers, as was expected.

Analysis calc'd for $C_{21}H_{25}FNO_5Li.0.65H_2O.65H_2O$: (MW:397.37+0.65 H$_2$O) C, 61.65; H, 6.48; N, 3.42; F, 4.64; Found: C, 61,52; H, 6.29; N, 3.55; F, 4.88.

IR Spectrum (KBr): $\mu_{max}$ 3392 cm$^{-1}$ (OH), 1675 cm$^{-1}$ (C=O, amide), 1586 cm$^{-1}$ (C=O, acid salt), 1509 cm$^{-1}$ (aromatic C=C), etc.

Mass spectrum: $(m+Li)^+ = 398$, $(m+Li-H)^- = 396$, $(m-H)^- = 390$, $(m+2Li-H)^+ = 404$ $H^1$-NMR Spectrum of Example 26 (DMSO-d$_6$, GX270): δ 0.86 (6 peaks, 6H, $H_{13}+H_{14}$), 1.46 (m, 1H, $H_{12}$), 1.67 (m, 1H, $H_9$), 1.82 (m, 2H, $H_4$), 2.04 (m, 3H, $H_2+H_{10a}$), 2.36 (dd, 1H, $H_{10b}$), 3.75 (m, 1H, $H_5$), 3.98 (d, 1H, J=15.5, $H_{15a}$), 4.19 (d, 1H, J=5.3, $H_8$), 4.38 (m, 1H, $H_3$), 4.77 (d, 1H, J=15.5, $H_{15b}$), 5.40 (broad, 1H, OH), 7.19 and 7.33 (two m, 4H, $H_{17}+H_{18}+H_{20}-H_{21}$)ppm.

EXAMPLE 27
(R*,S*)-7-[2-(4-Fluorophenyl)-3-oxo-2-azaspiro[4,4]-non-1-yl]-3,5-dihydroxy-6-heptenoic acid, monolithium salt

27-A. 2-(Cyclopentylidene)-acetic acid, ethyl ester

A suspension of hexane-washed 60% sodium hydride/paraffin (4.0 g, 100 mmol) in dry tetrahydrofuran was stirred (paddle stirrer) under an atmosphere of dry nitrogen in an icewater bath and a solution of triethyl phosphonoacetate (22.5 g, 100 mmol) in dry tetrahydrofuran (20 ml) was added dropwise in the course of 15 minutes. Soon a clear solution resulted. After 1.0 hour, a solution of cyclopentanone (8.4 g, 100 mmol) in dry tetrahydrofuran was added in the course of about 5.0 minutes. The cold water bath was then removed and the mixture was stirred at room temperature for 2.0 hours. The resulting mixture, which contained a large amount of gummy material at the bottom, was concentrated in vacuo, diluted with water (200 ml) and extracted with ether (3×75 ml). The extracts were combined, washed with brine (2×20 ml), dried over anhydrous magnesium sulfate, and concentrated. The residual oil was chromatographed over a column of silica gel (Baker 60–200 mesh, 70 g), eluting the column successively with hexane and etherhexane (5/95 and 10/90) to afford compound 27-A as a pleasant-smelling oil (13.0 g, 84.5%) with consistent $H^1$ and $C^{13}$ NMR spectra.

27-B. 2-(Cyclopentylidene)ethanol

A solution of Compound 27-A (5.04 g, 30 mmol) in toluene (40 ml) was added slowly into a stirred solution of 1.5M diisobutylaluminum hydride in toluene (60 ml, 90 mmol) in a Dry ice-acetone bath. The bath was then removed and the mixture was allowed to warm up to room temperature in the course of about 30 minutes. It was then added under stirring into a solution of sodium hydroxide (16 g, 400 mmol). The mixture was stirred for a few minutes and extracted with ether (3×70 ml). The extracts were combined, washed with brine (2×30 ml), dried over anhydrous magnesium sulfate and evaporated in vacuo to afford compound 27-B as a colorless oil (3.37 g, 100%) with consistent $H^1$ and $C^{13}$ NMR spectral data.

27-C. 1-Ethenyl-cyclopentane-1-acetic acid

A mixture of Compound 27-B [(2.8 g, 24.1 mmol), distilled· (b.p=142°)] triethylorthoacetate (27 ml, 150 mmol) and propionic acid (300 mg) was refluxed in an oil bath for 24 hours. A TLC examination showed the presence of three less polar compounds. The mixture was then cooled to ambient temperature and stirred for 24 hours with a mixture of methanol (35 ml), water (15 ml) and sodium hydroxide (2.0 g, 50 mmol). It was then concentrated in vacuo, diluted with brine (25 ml) and extracted with ether (3×20 ml). The aqueous solution was acidified with dilute hydrochloric acid to a pH of about 2.5, saturated with salt and extracted with ethyl acetate (3×20 ml). The extracts were combined, washed once with brine (15 ml) and evaporated to afford Compound 27-C as an oil (1.8 g, 50%) with consistent H¹ and C¹³ NMR spectral data.

Column chromatography of the ether extract containing non-acidic material on silica gel gave Compound 27-B (460 mg, 16.5%) and a mixture of three less polar compounds (300 mg), which were not characterized further.

27-D.
1-Ethenyl-1-cyclopentane-1-[N-(4-fluorophenyl)]-acetamide

To a stirred solution of Compound 27-C (1.5 g, 9.9 mmol) in dry dichloromethane (6.0 ml) in a bath at about 5° was added successively oxalyl chloride (1.3 ml, 1.9 g, 15 mmol) and a solution of dimethylformamide (0.2 ml) in dichloromethane (1.0 ml). Gas evolution was noted and eventually subsided. After 1.0 hour, the mixture was evaporated, initially under a jet of dry nitrogen and then in vacuo at about 35°. The residual oil, which contained some dark suspended solid, was dissolved in dry dichloromethane (25 ml), stirred, and a mixture of p-fluoroaniline (1.68 g, 15 mmol) and triethylamine (2.8 ml, 20 mmol) in dichloromethane (15 ml) was added. After 30 minutes, the mixture was added under stirring into 10% hydrochloric acid (50 ml), the organic layer was separated, and the aqueous layer was extracted with dichloromethane (2×25 ml). The organic solutions were combined, washed with brine (2×15 ml), dried over anhydrous magnesium sulfate and evaporated to afford crude compound 27-D as a solid. This product was chromatographed on silica gel (Baker 60-200 mesh, 25 g), eluting with dichloromethane-hexane mixtures (3/7, 1/1 and 7/3) to afford, after crystallization from ethyl acetate-hexane, Compound 27-D (2.13 g, 85%) as colorless needles, m.p. 93°–94° C., with consistent H¹ and C¹³ NMR spectral data.

27-E.
1-[(1,2-Dihydroxy)ethanyl]-cyclopentane-1-[N-(4-fluorophenyl)]-acetamide A solution of Compound 27-D (494 mg, 2.0 mmol), N-methylmorpholine oxide (282 mg, 2.4 mmol) and osmium tetroxide (25 mg) in a mixture of acetone (12 ml) and water (4.0 ml) was kept at room temperature for 4.0 hours. The mixture was then concentrated in vacuo, dissolved in ethyl acetate (60 ml) and washed successively with 10% hydrochloric acid and a 1N sodium hydroxide solution. The solution was then dried over anhydrous magnesium sulfate and evaporated to afford Compound 27-E as a homogeneous (TLC) colorless solid (560 mg, 100%), m.p. 71°–72° (from dichloromethane-hexane), Rf=0.37 (Merck silica gel plates, ethyl acetate), with consistent H¹ and C¹³ NMR spectral data.

27-F.
2-[(4-Fluorophenyl)-3-oxo-2-azaspiro(4,4)-non-1-yl]-methanol

A solution of Compound 27-E (2.59 g, 9.2 mmol) in dry pyridine (20 ml) containing 4-dimethylaminopyridine (25 mg) was stirred under an atmosphere of dry nitrogen in an ice bath and a solution of p-toluene sulfonyl chloride (1.91 g, 10 mmol) in dry pyridine (5.0 ml) was added in the course of 3 minutes. After 45 minutes, TLC examination (of an aliquot washed with dilute hydrochloric acid in dichloromethane solution) showed that almost all of the starting diol compound 27-E had disappeared and essentially a single less polar product was present. After 1¼ hours, dry tetrahydrofuran (20 ml) was added followed by potassium t-butoxide (2.47 g, 22 mmol). The mixture was then stirred in the ice bath for 30 minutes and at room temperature for 20 hours. It was then concentrated in vacuo, diluted with 1.0N hydrochloric acid, saturated with salt and extracted with ethyl acetate (3×60 ml). The extracts were combined, washed with a dilute sodium bicarbonate solution and brine, dried over anhydrous magnesium sulfate and evaporated to afford the crude product as a semi-solid (2.42 g).

A TLC examination (silica gel, ethyl acetate) of this crude product showed that essentially six compounds were present. Two of these had mobilities close to the intermediate monotosylate, two had mobilities close to the starting diol (Compound 27-E) and two were in between. Of these last two spots (approximately 8/2 ratio), the more polar major one was Compound 27-F. One crystallization of the crude material from ethyl acetate-hexane gave homogeneous (TLC) compound 27-F as essentially colorless crystals (787 mg). Flash chromatography of the material in the mother liquor using ethyl acetate-hexane 1:1 and 7:3 gave another 275 mg of Compound 27-F, increasing the total yield to 43.9%. It showed m.p. 139°–141° (ethyl acetate-hexane), Rf=0.5 (Merck silica gel plates, ethyl acetate) and consistent H¹ and C¹³ NMR spectral data.

27-G.
2-[(4-Fluorophenyl)-3-oxo-2-azaspiro(4,4)-non-1-yl]carboxaldehyde

A solution of Compound 27-F (500 mg, 1.9 mmol) in dry dichloromethane containing dry t-butanol (4 drops) was stirred with Dess-Martin Periodinane (848 mg, 2.0 mmol) at ambient temperature for 1.0 hour. It was then added into a 0.5M sodium thiosulfate solution (30 ml) containing sodium bicarbonate (2.0 g) until the two layers were clear. The dichloromethane layer was separated, washed once with brine, dried over anhydrous magnesium sulfate and evaporated to afford crude Compound 27-G as a solid. Purification by column chromatography (Baker 60–200 mesh silica gel using dichloromethane-hexane, 1:1 and dichloromethane for elution) gave homogeneous (TLC) Compound 27-G as a solid (390 mg, 78.6%), Rf=0.67 (Merck silica gel plate, ethyl acetate) with consistent H¹ and C¹³ NMR spectral data.

27-H.
(R,S)-7-[2-(4-Fluorophenyl)-3-oxo-2-azaspiro-[4,4]-non-1-yl]-3-[[(1,1-dimethylethyl)dimethylsilyl]oxy]-5-oxo-6-heptenoic acid, methylester To a stirred mixture of compound 27-G (387 mg, 1.48 mmol), lithium chloride (70 mg, 1.65 mmol) and the chiral betaketophosphonate compound 1-O (630 mg, 1.65 mmol) in dry acetonitrile (3.5 ml) was added a solution of 1,8-diazabicyclo[5,4,0]undec-7-ene (228 mg, 1.5 mmol) in acetonitrile (2.5 ml). The solution soon became turbid. After 1¾ hours, it was added into a 10% potassium hydrogen sulfate solution (50 ml) which was then extracted with dichloromethane (3×20 ml). The extracts were combined, washed with brine, dried over anhydrous magnesium sulfate, evaporated and the residual oil was chromatographed on a column of silica gel (Baker 60–200 mesh, 20 g), eluting the column with dichloromethane-hexane (1:1), dichloromethane and dichloromethane-ethyl acetate mixtures to afford Compound 27-H as a homogeneous (TLC) oil (680 mg, 88.9%), Rf=0.75 (Merck silica gel plates, ethyl acetate) with consistent H¹ and C¹³ NMR spectral data.

Since Compound 27-G is racemic and Compound 1-O is optically pure, two chiral diastereomers are expected in Compound 27-H. These were not distinguishable in the H¹ and C¹³ NMR spectra at 270 Mz in CDCl₃. They were also not readily separable by TLC.

27-I.
(R,S)-7-[2-(4-Fluorophenyl)-3-oxo-2-azaspiro-[4,4]-non-1-yl]-3-hydroxy-5-oxo-6-heptenoic acid, methylester A solution of Compound 27-H (660 mg, 1.28 mmol) in acetonitrile (5.0 ml) was stirred for 2.0 hours with 48% hydrofluoric acid (0.3 ml) in a bath at about 5°. It was then added into brine (50 ml), which was extracted with ethyl acetate (3×20 ml). The extracts were combined, washed with a dilute sodium bicarbonate solution and brine, dried over anhydrous magnesium sulfate and evaporated to afford the crude product as an oil. This product was chromatographed on a column of silica gel (Baker 60-200 mesh, 20 g), eluting the column with dichloromethane and dichloromethane-ethyl acetate mixtures (9:1, 4:1 and 7:3) to afford homogeneous (TLC) Compound 27-I as a thick oil (490 mg, 95.2%), Rf=0.6 (Merck silica gel, ethyl acetate) with consistent H¹ and C¹³ NMR spectral data.

The two chiral diastereoisomeric compounds expected in Compound 27-I were not readily separable by chromatography. They also could be distinquished from the 270 MHz NMR spectra in CDCl₃.

27-J.
(R*,S*)-7-[2-(4-Fluorophenyl)-3-oxo-2-azaspiro-[4,4]-non-1-yl]-3,5-dihydroxy-6-heptenoic acid, methylester A solution of Compound 27-I (440 mg, 1.09 mmol), 1.0M triethylborane in tetrahydrofuran (1.7 ml) and pivalic acid (10 mg) in dry tetrahydrofuran (4.0 ml) was stirred under an atmosphere of dry nitrogen for 30 minutes. The solution was then cooled in a dry ice-acetone bath at −78° and solid sodiumborohydride (53.3 mg, 1.4 mmol) was added followed dropwise by dry methanol (1.1 ml). After 1½ hours, a solution of 30% hydrogen peroxide (1.75 ml) in water (3.0 ml) was added cautiously (gas evolution), the mixture was warmed to ambient temperature and was stirred for 1.0 hour. It was then added into 1.0N hydrochloric acid (5.0 ml), diluted with brine (25 ml) and extracted with ethyl acetate (3×15 ml). The extracts were combined, washed once with brine and a dilute sodium bicarbonate solution, dried over anhydrous magnesium sulfate and evaporated to afford the crude product as a thick oil. This crude product was chromatographed on a column of silica gel (Baker 60-200 mesh, 15 g), eluting the column with dichloromethane and dichloromethane-ethyl acetate mixtures (9:1 and 4:1) and ethyl acetate to afford homogeneous (TLC) Example 27 as a thick oil (389 mg, 88%), Rf=0.3 (Merck silica gel, ethyl acetate) with consistent H¹ and C¹³ NMR spectral data.

The two chiral diastereomers present in Example 27 in nearly equal amounts were partially separable by TLC on Merck silica gel plates after two developments of the plate. While these could not be distinguished from the H¹ NMR spectrum at 270 MHz in CDCl₃, split peaks were observed for C-3 and C-5 and two more carbons (presumably C-2 and C-4), suggesting the presence of two diastereomers.

EXAMPLE 28
(R*,S*)-7-[2-(4-Fluorophenyl)-3-oxo-2-azaspiro-[4,4]nonyl]-3,5-dihydroxy-6-heptenoic acid, monolithium salt A solution of Example 28 (194 mg, 0.479 mmol) in tetrahydrofuran (3.0 ml) was stirred with 1.0N lithium hydroxide under an atmosphere of nitrogen at ambient temperature for 40 minutes. It was then concentrated in vacuo, diluted with deionized water (10 ml) and applied on an HP-20 column (4"×1" column bed), which was eluted successively with deionized distilled water (200 ml) and deionized distilled water-methanol (1:1, 200 ml). The latter eluate was evaporated in vacuo and lyophilized to afford Example 28 as a colorless powder (195 mg, 95%) with consistent elemental analysis and mass, infrared and H¹ NMR spectral data.

Analysis calc'd for $C_{21}H_{25}FLiNO_5$ (MW 397.37/0.57H₂O): C, 61.66; H, 6.46; N, 3.44; F, 4.66%. Found: C, 61.94; H, 6.36; N, 3.36; F, 4.48%.

IR Spectrum (KBr): $\mu_{max}$ 3400 cm⁻¹ (strong, OH), 1682 cm⁻¹ (strong, amide C=O), 1588 cm⁻¹ (strong, salt C=O), 1510 cm⁻¹ (strong, aromatic C=C) etc.

H¹-NMR Spectrum (DMSO-d₆, FX-270): δ1.1 to 2.1 (m, 10H, H₄ and H₁₂ to H₁₅), 1.8, 1.98 (m, 2H, H₂), 2.4 (AB quartet, 2H, J=16.5, H₁₀), 3.6 (m, 1H, H₈), 4.1 (q, 1H, J=~8.0, 4.0, H₃), 4.38 (q, 1H, J=~4.0, 2.0, H₅), 4 90 (m, 1H, OH), 5.58 (m, 2H, H₆ and H₇), 7.15 and 7.52 (m, 4H, aromatic H) ppm.

EXAMPLE 29
(R*,S*)-7-[2-(4-Fluorophenyl)-3-oxo-2-azaspiro[4,4]-non-1-yl]-3,5-dihydroxy heptanoic acid, methylester A solution of Example 27 (194 mg, 0.479 mmol) in ethyl acetate (4.0 ml) was stirred under an atmosphere of hydrogen with 10% palladium on carbon for 2.5 hours. The mixture was then filtered through a bed of Celite, washing the Celite with ethyl acetate, and the combined filtrate and washings was evaporated in vacuo to afford Example 29 as a homogeneous (TLC) thick oil (195 mg, 100%), Rf=0.27 (ethyl acetate, silica gel), with consistent H¹ and C¹³ NMR spectral data.

Since Example 28 was a mixture of two chiral diastereomers (about 1:1), Example 29 was expected to be a mixture (about 1:1) of two diastereomers. These were not readily separable by TLC (silica gel, ethyl acetate). No difference was noted between the two diastereomers in the H¹ NMR spectrum at 270 MHz. In the C¹³ NMR spectrum, however, some of the peaks, particularly C₃ or C₅, were split suggesting the presence of two diastereomers.

EXAMPLE 30
(R*,S*)-7-[2-(4-Fluorophenyl)-3-oxo-2-azaspiro[4,4]-non-1-yl]-3,5-dihydroxyheptanoic acid, monolithium salt A solution of Example 29 (195 mg, 0.479 mmol) in tetrahydrofuran (3.0 ml) was stirred under an atmosphere of nitrogen at ambient temperature with 1.0N lithium hydroxide for 45 minutes. The mixture was then concentrated in vacuo, diluted with deionized water and applied on a column of HP-20 (3"×1.5" bed). The column was successively eluted with deionized distilled water (200 ml) and deionized distilled water-methanol (1:1, 200 ml). The latter eluate which contained Example 30 by TLC was evaporated in vacuo and lyophilized to afford the analytical specimen of Example 30 as a colorless powder (180 mg, 94%), Rf=0.34 (silica gel; ethyl acetate-hexane-acetic acid, 8:2:1) with consistent mass, infrared and H¹-NMR spectral data.

Analysis calc'd for $C_{21}H_{27}FNO_5Li$ (399.38. 0.50 $H_2O$): C, 61.76; H, 6.91; N, 3.43; F, 4.65%. Found: C, 61.78; H, 6.87; N, 3.29; F, 4.41%.

IR Spectrum (KBr): $\mu_{max}$ 1681 cm$^{-1}$ (strong, amide C=O), 1589 cm$^{-1}$ (strong, acid salt C=O), 1510 cm$^{-1}$ (strong, aromatic C=C) etc. H¹ NMR Spectrum (DMSO-d$_6$, FX-270):

δ 1.20, 1.70 (m, 14 H, $H_4$, $H_6$, $H_7$ and $H_{12}$ to $H_{15}$, ~1.8 and 1198 (m, 2H, $H_2$), 2.15 and 2.57 (AB quartet, J= ~16.8, $H_{10}$), 3.35 (broad m, $H_8$+OH+$H_2O$), 3.70 (m, 1H, $H_5$), 4.00 (broad s, 1H, $H_3$) and, 7.20, 7.52 (m, 2H each, aromatic H) ppm.

EXAMPLE 31

(3R*,5S*,6E,trans)-7-[1-(4-Fluorophenyl)-3-(1-methylethyl)-5-oxo-2-pyrrolidinyl]-3,5-dihydroxy-6-heptenoic acid, monolithium salt

31-A. E-4-Methyl-3-pentenol

To a stirred solution of Example 31 (25 g, 175.82 mmol) in tetrahydrofuran (50 ml) at −78° (Dry ice-acetone bath) under an atmosphere of nitrogen was added a solution of 1.0M diisobutyl aluminum hydride in hexane (386.8 ml, 386.8 mmol) and then the solution was allowed to warm up to room temperature. After 1.0 hour, brine (300 ml) was added, the mixture was stirred for 30 minutes and extracted with ethyl ether (3×200 ml). The combined ethyl ether extracts were washed with brine, dried over anhydrous magnesium sulfate and evaporated in vacuo to give an oil (20 g). This oil was passed through a column of silica gel (200 g, Baker 60-200 mesh) eluting with ethyl ether-hexane (1.9) to give 17 g (96.6%) of homogeneous (TLC, Rf=0.5, silica gel, 1:1 ethyl acetate-hexane) compound 31-A as an oil with consistent H¹-NMR and C¹³-NMR spectra.

31-B. 3-Ethenyl-4-methyl-pentanoic acid

A mixture of compound 31-A (10 g, 100 mmol), triethyl orthoacetate (108 ml, 600 mmol) and propionic acid (1.2 g) was refluxed in an oil bath for 72 hours. A TLC examination showed the absence of compound 31-A and the presence of one single less polar compound. The mixture was cooled to room temperature, methanol (50 ml), water (50 ml) and sodium hydroxide (10 g, 250 mmol) were added and the mixture refluxed for 4 hours under stirring. It was then concentrated in vacuo, diluted with brine (50 ml) and extracted with ethyl ether (3×30 ml). The aqueous solution was acidified with concentrated hydrochloric acid to a pH of about 2.5, saturated with sodium chloride and extracted with ethyl acetate (4×50 ml). The combined ethyl acetate extracts were washed with brine, dried over anhydrous magnesium sulfate and evaporated in vacuo to give 8.5 g (59.95) of homogeneous (TLC, Rf=0.25, silica gel, 1:1 ethyl acetate hexane) compound 31-B as a thick oil with consistent H¹-NMR and C¹³-NMR spectra.

31-C 3-Ethenyl-4-methyl-N-(4-fluorophenyl)pentanamide

To a stirred solution of compound 31-B (8.5 g, 59.78 mmol) in dry dichloromethane (40 ml) in an ice bath under an atmosphere of nitrogen was added successively oxalyl chloride (7.82 ml, 89.67 mmol) and dimethylformamide (1 ml). The solution was gradually warmed up to room temperature. After 1 hour, the solvent was evaporated by a stream of nitrogen and the residue was dried in vacuo at room temperature for a few minutes. The residual oil was dissolved in dry dichloromethane (50 ml), stirred, and a mixture of 4-fluoroaniline (8.49 ml, 89.67 mmol) and triethylamine (16.7 ml, 119.56 mmol) in dichloromethane (30 ml) was added dropwise. After 30 minutes, the mixture was slowly poured into 10% hydrochloric acid under stirring. The organic layer was separated and the aqueous layer was extracted with dichloromethane (2×100 ml). The combined dichloromethane extracts were washed with brine, dried over anhydrous magnesium sulfate and evaporated in vacuo to afford crude compound 31-C as a thick oil. This oil was chromatographed on a column of silica gel (200 g, Baker 60-200 mesh), eluting with dichloromethane-hexane (3:7 and 1:1) to give 8.0 g (56.9%) of homogeneous (TLC, silica gel, Rf=0.4, 1:1 ethyl acetate-hexane) compound 31-C as a solid, m.p. 74°-75°, with consistent H¹-NMR and C¹³-NMR spectra.

31-D. 3-(1-Methylethyl)-4,5-dihydroxy-N-(4-fluorophenyl)-pentanamide

A solution of compound 31-C (8.0 g, 34 mmol), N-methylmorpholine oxide (5.26 g, 45 mmol) and osmium tetroxide (180 mg) in a mixture of acetone (40 ml) and water (20 ml) was stirred at room temperature under an atmosphere of nitrogen for 72 hours. The mixture was then concentrated in vacuo, dissolved in ethyl acetate (250 ml), washed successively with 10% hydrochloric acid, a 1N sodium hydroxide solution and brine, dried over anhydrous magnesium sulfate and evaporated in vacuo to give a gum. This gum was passed through a column of silica gel (2.5"×1.5" column bed, Baker 60-200 mesh) eluting with ethyl acetatehexane (1:1) and ethyl acetate to give 5.7 g (62.2%) of TLC-homogeneous (Rf=0.15, silica gel, 1:1 ethyl acetate-hexane) compound 31-D as a solid, m.p. 112°-113°, with consistent H¹-NMR and C¹³-NMR spectra. In addition, unreacted Compound 31-C was also isolated.

31-E. trans-1-[(4-Fluorophenyl)-3-(1-methylethyl)-5-oxo-2-pyrrolidinyl]-2-methanol A solution of compound 31-D (3 g, 11.14 mmol) in dry pyridine (20 ml) containing 4-dimethylaminopyridine (35 mg) was stirred under an atmosphere of nitrogen in an ice bath and a solution of p-toluenesulfonyl chloride (2.34 g, 12.25 mmol) in dry pyridine (10 ml) was added dropwise. After 45 minutes, TLC examination showed that almost all Compound 31-D had disappeared and essentially a single less polar product was present. Dry tetrahydrofuran (30 ml) was then added, followed by potassium t-butoxide (3.13 g, 27.85 mmol). The mixture was then stirred in the ice bath for 1 hour and at room temperature for 20 hours. It was then concentrated in vacuo, diluted with 1.0N hydrochloric acid, saturated with sodium chloride and extracted with ethyl acetate (3×60 ml). The combined ethyl acetate extracts were washed with a saturated sodium carbonate solution and brine, dried over anhydrous magnesium sulfate and evaporated in vacuo solution to give an oil. This oil was chromatographed on a column of silica gel (75 g, Baker 60-200 mesh) eluting with ethyl acetatehexane (1:9 and 1:4) to give three major products. The three major products were in order of increasing polarity (silica gel, ethyl acetate), N-(4-fluorophenyl)-4-(1-methylethyl)-5-hydroxy-piperidine-2-one (620 mg) the 3,4-cis-pyrrolidinone (isomer of compound 31-E; 280 mg) and 3,4-trans-pyrrolidinone (compound 31-E; 820 mg). Column chromatography of this gave Compound 31-E (820 mg, 29.2%), a solid (m.p. 44°–45°), with consistent H$^1$-NMR and C$^{13}$-NMR spectra.

31-F.
trans-1-[(4-Fluorophenyl)-3-(1-methylethyl)-5-oxo-2-pyrrolidine]-2-carboxaldehyde To a stirred suspension of Dess-Martin periodinane (928 mg, 2.19 mmol) in dichloromethane (8 ml) at room temperature under an atmosphere of nitrogen was added a solution of compound 31-E (500 mg, 2.99 mmol) in dichloromethane (4 ml) followed by t-butanol (206 μl, 2.19 mmol). After 1 hour, the mixture was poured into a stirred mixture of sodium bicarbonate (2 g., 23.81 mmol) in 0.5M sodium thiosulfate (30 ml) and dichloromethane (50 ml). The mixture was stirred vigorously until the two layers were clear. The dichloromethane layer was separated, washed with brine, dried over anhydrous magnesium sulfate and evaporated in vacuo to give 470 mg (94.8%) of Compound 31-F as a homogeneous (TLC, Rf=0.55, silica gel, ethyl acetate) oil, with consistent H$^1$-NMR and C$^{13}$-NMR spectra. This oil was used in the next step without chromatographic purification.

31-G.
(3R,6E,trans)-7-[1-(4-Fluorophenyl)-3-(1-methylethyl)-5-oxo-2-pyrrolidinyl]-3-[[(1,1-dimethylethyl)dimethylsilyl]-oxy]-5-hydroxy-6-heptenoic acid, methylester To a stirred mixture of compound 31-F (470 mg, 1.89 mmol), lithium chloride (103 mg, 2.45 mmol) and the chiral compound 1-O (828 mg, 2.17 mmol) in dry acetonitrile (7 ml) at room temperature under an atmosphere of nitrogen was added a solution of 1,8-diazo-bicyclo-[5,4,0]-undec-7-ene (287 mg, 1.89 mmol) in dry acetonitrile 92 ml). After 4 hours, dichloromethane (100 ml) was added. The solution was washed with a 10% potassium hydrogen sulfate solution and brine, dried over anhydrous magnesium sulfate and evaporated in vacuo to give an oil. This oil was chromatographed on a column of silica gel (40 g, Baker 60-200 mesh), eluting with dichloromethaneethyl acetate (95:5) to give 680 mg (71.3%) of homogeneous (TLC, Rf=0.75, silica gel, ethyl acetate) compound 31-G as an oil with consistent H$^1$-NMR and C$^{13}$-NMR spectra. Since compound 31-F was racemic and compound 1-O was optically pure, two chiral diastereomers were present in compound 31-G. These two diastereomers were not readily distinguishable by H$^1$-NMR (270 MHz, CDCl$_3$) or TLC.

31-H.
(3R,6E,trans)-7-[1-(4-Fluorophenyl)-3-(1-methylethyl)-5-oxo-2-pyrrolidinyl]-3-hydroxy-5-oxo-6-heptenoic acid, methylester To a stirred and chilled (ice bath) solution of compound 31-G (680 mg, 1.345 mmol) in acetonitrile (15 ml) under an atmosphere of nitrogen was added dropwise 48% hydrofluoric acid. After 1.0 hour at 0°, water (5 ml) was added followed by sodium bicarbonate (1.5 g). The mixture was warmed up to room temperature, stirred for 30 minutes, diluted with brine (15 ml) and extracted with ethyl acetate (4×30 ml). The combined ethyl acetate extracts were washed with brine, dried over anhydrous magnesium sulfate and evaporated in vacuo to give a gum. This gum was chromatographed on a column of silica gel (40 g, Baker 60-200 mesh), eluting with ethyl acetate-dichloromethane (1:9, 1:4 and 1:1) to give 490 mg (93.1%) of homogeneous (TLC, Rf=5, silica gel, ethyl acetate) compound 31-H as an oil with consistent H$^1$-NMR and C$^{13}$-NMR spectra.

31-I.
(3R,5S,6E,trans)-7-[1-(4-Fluorophenyl)-3-(1-methylethyl)-5-oxo-2-pyrrolidinyl]-3,5-dihydroxy-6-heptenoic acid, methylester A mixture of compound 31-H (490 mg, 1.25 mmol), triethylborane (1.0M solution in tetrahydrofuran, 1.88 ml, 1.88 mmol) and pivalic acid (10 mg) in dry tetrahydrofuran (6 ml) was stirred for 30 minutes at room temperature under an atmosphere of nitrogen and then cooled to −78° (dry ice-acetone bath). Sodium borohydride (59.2 mg, 1.56 mmol) was added followed dropwise by dry methanol (4.5 ml). After 2 hours, a solution of 30% hydrogen peroxide (6 ml) in water (4 ml) was added dropwise (gas evolution). The mixture was then warmed up to room temperature, stirred for 1.0 hour and acidified with 5% hydrochloric acid to a pH of 3. After another hour, the organic solvent was evaporated in vacuo. The residual slurry was diluted with brine (30 ml) and extracted with ethyl acetate (4×30 ml). The combined ethyl acetate extracts were washed with brine, dried over anhydrous magnesium sulfate and evaporated in vacuo to give a gum. This gum was chromatographed on a column of silica gel (40 g, Baker 60-200 mesh), eluting successively with ethyl acetate-dichloromethane (1:4 and 1:1) to give 410 mg (83.2%) of Example 31 as a gum with consistent H$^1$-NMR and C$^{13}$-NMR spectra.

EXAMPLE 32
(3R*,5S*,6E,trans)-7-[1-(4-Fluorophenyl)-3-(1-methylethyl)-5-oxo-2-pyrrolidinyl]-3,5-dihydroxy-6-heptenoic acid, monolithium salt A stirred solution of Example 31 (200 mg, 0.508 mmol) in tetrahydrofuran (4 ml) at room temperature under an atmosphere of nitrogen was treated with 1.0N lithium hydroxide (0.56 μl, 0.56 mmol). After 1.0 hour, the solvent was evaporated in vacuo to give a gum. This gum was chromatographed on a column of HP-20 (1"×1" column bed) eluting with deionized, distilled water (250 ml) and 30% methanol-water (250 ml) to give in the latter eluate TLC-homogeneous Example 32. This latter eluate was evaporated in vacuo and lyophilized overnight to give 120 mg (61.3%) of a hydrated analytical specimen of Example 32 (as a white solid with consistent IR, mass and H$^1$-NMR spectral data.

Analysis calculated for $C_{20}H_{25}FNO_5 \cdot Li \cdot 0.2H_2O$: C, 61.76; H, 6.58; N, 3.60; F, 4.88. Found: C, 61.72; H, 6.70; N, 3.64; F, 4.88.

IR Spectrum (KBr): $\mu_{max}$ 3424 cm$^{-1}$ (OH), 1677 cm$^{-1}$ (C=O, amide), 1585 cm$^{-1}$ (C=O, acid salt), 1509 cm$^{-1}$ (aromatic c=c).

Mass: (M+Li)$^+$=386, (M+3Li−2H)$^+$=398, (M−H)$^-$=378, (M+Li−=2H)$^-$=384 (M+2Li−H)$^+$=392, (M+2Li−3H)$^-$=390

H$^1$-NMR Spectrum of Example 32 (DMSO−d$_6$, GX270): δ 0.92 (d,6H,J=~8.0,H$_{13}$+H$_{14}$), 1.16 (m,1H,H$_{12}$) 1.39 (m,1H,H$_9$), 1.77 (m,2H,H$_4$), 1.95

(m,2H,H$_2$), 2.02 (dd,1H,H$_{10a}$), 2.60 (dd,1H,H$_{10b}$), 3.50, 3.62 (m,1H,H$_8$), 4.06 (m,1H,H$_5$), 4.45 (m,1H,H$_3$), 4.88 (broad,1H,OH), 5.42 and 5.62 (2m,2H,H$_6$+H$_7$), 7.15 and 7.45 (2m,4H,H$_{16}$+H$_{17}$+H$_{19}$+H$_{20}$)ppm.

EXAMPLE 33

(3R,5S,trans)-1-(4-Fluorophenyl)-3,5-dihydroxy-3-(1-methylethyl)-5-oxo-2-pyrrolidine-heptanoic acid, methylester A solution of Example 31 (200 mg, 0.51 mmol) in ethyl acetate (20 ml) containing 10% palladium on carbon was hydrogenated at atmospheric pressure at room temperature for 3 hours. It was then filtered through a bed of Celite and washed with a small amount of ethyl acetate. The filtrate and washing were combined and evaporated in vacuo to give a gum. This gum was chromatographed on a column of silica gel (25 g, Baker 60–200 mesh) eluting with ethyl acetate-dichloromethane (1:3 and 1:1) to give 180 mg (89.5%) of Example 33 (Rf=0.4, silica gel, ethyl acetate) as a gum with consistent H$^1$-NMR and C$^{13}$-NMR spectra. The two chiral diastereomers present in Example 33 in nearly equal amounts are partially separable by TLC (silica gel, ethyl acetate). They are not distinquishable by the H$^1$-NMR (270 MHz, CDCl$_3$) spectrum.

EXAMPLE 34

(3R,5S,trans)-1-(4-Fluorophenyl)-3,5-dihydroxy-3-(1-methylethyl)-5-oxo-2-pyrrolidine-heptanoic acid, monolithium salt A stirred solution of Example 33 (180 mg, 0.455 mmol) in tetrahydrofuran (4 ml) at room temperature under an atmosphere of nitrogen was treated with 1.0N lithium hydroxide (501 μl, 0.501 mmol). After 1.0 hour, the solvent was evaporated in vacuo to give a gum. This gum was dissolved in water and chromatographed on a column of HP-20 (1"×1" column bed), eluting with deionized, distilled water (about 250 ml) and 30% methanol-water (about 250 ml) to give in the later eluate TLC-homogeneous Example 34. This eluate was evaporated in vacuo and lyophilized overnight to give 120 mg (68.1%) of a hydrated analytical specimen of Example 34 as a white solid with consistent IR, mass and H$^1$-NMR spectral data. The two chiral diastereomers present were not distinguishable by TLC (silica gel, 8:1:1 dichloromethane-methanol-acetic acid) and H$^1$-NMR (270 MHz, DMSO-d$_6$).

Analysis calc'd for C$_{20}$H$_{27}$FNO$_5$Li.0.54H$_2$O (MW: 37=87.38+0.54 H$_2$O): C, 60.50; H, 7.13; N, 3.53; F, 4.79; Found: C, 60.49; H, 7.19; N, 3.54; F, 4.83.

IR Spectrum (KBr): $\mu_{max}$ 3407 cm$^{-1}$ (OH), 1676 cm$^{-1}$ (C=O, amide), 1586 cm$^{-1}$ (C=O, acid salt), 1510 cm$^{-1}$ (aromatic, C=C)

Mass spectrum: (M+Li)$^+$+Li=394, (M+Li)$^+$+-2Li=400, (M−H)$^-$=380, (M−H)$^-$+Li=386

H$^1$-NMR spectrum of Example 34 (DMSO-d$_6$, GX270): δ 0.90 (d, 6H, J=~8.0, H$_{13}$+H$_{14}$), 1.98 (m, 2H, H$_2$), 2.16 (dd, J=17.9, 2.9, 1H, H$_{10a}$), 2.73 (dd, J=17.5, 7.6 1H, H$_{10b}$), 3.74 (m, 1H, H$_3$), 4.05 (m, 1H, H$_5$), 7.20 and 7.55 (2m, 4H, H$_{16}$+H$_{17}$+H$_{19}$+H$_{20}$) ppm.

EXAMPLE 35

(5R*,3S*,trans)-7-[1-[(4-Fluorophenyl)methyl]-3-(1-methylethyl)-5-oxo-2-pyrrolidinyl]-3,5-dihydroxy-6-heptynoic acid, methylester

35-A.
trans-1-[(4-Fluorophenyl)methyl]-3-(1-methylethyl)-5-oxo-pyrrolidine-2-methanol To absolute dry ethanol (10 mL) was added sodium (30 mg) under an atmosphere of nitrogen. After the sodium completely dissolved, a solution of compounds 17-D and 17-E (300 mg, 0.98 mmol, a mixture of 2,3-cis and trans isomers, in dry ethanol (2 mL) was added. The mixture was heated at 55° C. (oil bath temperature) for 24 hours, acidified with 10% hydrochloric acid to a pH of 3 and evaporated in vacuo to give a gum. This gum was diluted with brine (15 mL) and extracted with ethyl acetate (3×20 mL). The combined ethyl acetate extracts were washed with brine, dried over anhydrous magnesium sulfate and evaporated in vacuo. The gummy residue was chromatographed on a column of silica gel (LPS-1, 60 g), eluting with ethyl acetate-hexane (1:4) to give thin layer chromatography-homogeneous compound 17-E trans isomer (240 mg, 91.7%) with consistent $^1$H-NMR and $^{13}$C-NMR spectra. Another run using 600 mg of the mixture of compounds 17-D and 17-E gave 500 mg more of compound 17-E.

To a chilled (ice bath) and stirred suspension of lithium borohydride (465 mg, 21.38 mmol) in dry tetrahydrofuran (12 ml) under an atmosphere of nitrogen was added dropwise a solution of compound 17-E (730 mg, 2.375 mmol) in tetrahydrofuran (3 mL). The mixture was gradually warmed to room temperature and dry methanol (0.77 mL, 19 mmol) was added dropwise. After 20 hours, the resulting mixture was slowly poured into 5% hydrochloric acid and stirred for 30 minutes. The tetrahydrofuran and methanol were removed in vacuo. The residue was diluted with brine (35 mL) and extracted with ethyl acetate (3×50 mL). The combined ethyl acetate extracts were washed with a saturated sodium bicarbonate solution, dried over anhydrous magnesium sulfate and evaporated in vacuo to give a gummy residue. This residue was chromatographed on a column of silica gel (Baker 60-200 mesh, 50 g) eluting with ethyl acetate-hexane (1:1) to give 520 mg (82.6%) of thin layer chromatography-homogeneous compound 35-A as a gum with consistent $^1$H-NMR and $^{13}$C-NMR spectra.

35-B.
trans-1-[(4-Fluorophenyl)methyl]-3-(1-methylethyl)-5-oxo-pyrrolidine-2-carboxaldehyde To a stirred suspension of Dess-Martin periodinane (915 mg, 2.16 mmol) in dichloromethane (10 mL) at room temperature under an atmosphere of nitrogen was added dropwise a solution of compound 35-A (520 mg, 1.96 mmol) in dichloromethane (5 mL) followed by t-butyl alcohol (203 μl, 2.16 mmol). After 1 hour, the mixture was poured into a mixture of sodium bicarbonate (1.5 g) in 0.5 M sodium thiosulfate solution (22 mL) and dichloromethane (80 mL). The mixture was stirred vigorously until the two layers were clear. The dichloromethane layer was separated, washed with brine, dried over anhydrous magnesium sulfate and evaporated in vacuo to give 490 mg (94.9%) of compound 35-B as an oil, with consistent $^1$H-NMR and $^{13}$C-NMR spectra. This material was used in the next step without purification.

35-C.
trans-1-[[(4-Fluorophenyl)methyl]-3-(1-methylethyl)-5-oxo-2-pyrrolidinyl]-ethyne To a chilled (−40° C., acetonitrile-dry ice) and stirred suspension of potassium t-butoxide (313 mg, 2.79 mmol) in dry tetrahydrofuran (12 mL) under an atmosphere of nitrogen was added dropwise a solution of diethyl diazomethylphosphonate (500 mg, 2.79 mmol) in dry tetrahydrofuran (3 mL). (Diethyldiazomethylphosphonate was prepared by the composite procedure of D. Seyferch et al., J. Org. Chem., 36, (1971), 1384 and S. K. Davidsen, et al., Org. Synth. 65 (1987), 119. After 1.0 hour, a solution of compound 35-B (490 mg, 1.86 mmol) in tetrahydrofuran (3 mL) was added dropwise. After 3.0 hours, a 10% potassium hydrogen sulfate solution (20 mL) was added. The mixture was warmed up to room temperature, stirred for 20 minutes, diluted with brine (30 mL) and extracted with dichloromethane (3×50 mL). The combined dichloromethane extracts were washed with a 10% potassium hydrogen sulfate solution and brine, dried over anhydrous magnesium sulfate and evaporated in vacuo to give an oil. This oil was chromatographed on a column of silica gel (Baker 60-200 mesh, 60 g), eluting with ethyl acetate-hexane (2:8) to give 385 mg (79.6%) of thin layer chromatography-homogeneous compound 35-C (silica gel, 1:1 ethyl acetate-hexane, $R_f$=0.4) as a gum with consistent $^1$H-NMR and $^{13}$C-NMR spectra.

35-D.
trans-1-[3-[(4-Fluorophenyl)methyl]-3-(1-methylethyl)-5-oxo-2-pyrrolidinyl]-3-butynol To a chilled (−78° C, dry ice-acetone bath) and stirred solution of compound 35-C (385 mg, 1.485 mmol) in tetrahydrofuran (4 mL) under an atmosphere of nitrogen was added dropwise n-n-butyl lithium (2.3 M solution in hexane, 645 μl, 1.61 mmol). After 45 minutes, dry paraformaldehyde (223 mg, 7.43 mmol) was added. The mixture was stirred for 2 hours at −78°, 2 hours at 0° and 18 hours at room temperature. Brine (25 mL) was added and the resulting slurry was extracted with ethyl acetate (3×25 mL). The ethyl acetate extracts were washed with water, dried over anhydrous magnesium sulfate and evaporated in vacuo to give an oil. This oil was chromatographed on a column of silica gel (Baker 60-200 mesh, 35 g), eluting successively with ethyl acetate-hexane mixture (1:9 and 1:3) to give 320 mg (74.6%) of thin layer chromatography-homogeneous compound 35-D (silica gel, 1:1 ethyl-hexane, $R_f$=0.15) as an oil with consistent $^1$H-NMR and $^{13}$C-NMR spectra.

35-E.
trans-1-[3-[(4-Fluorophenyl)methyl]-3-(1-methylethyl)-5-oxo-2-pyrrolidinyl]-3-butynal To a stirred suspension of Dess-Martin periodinane (518 mg, 1.22 mmol) in dichloromethane (4 mL) at room temperature under an atmosphere of nitrogen was added dropwise a solution of compound 35-D (320 mg, 1.11 mmol) in dichloromethane (2 mL), followed by t-butyl alcohol (115 μl, 1.22 mmol). After 1 hour, the mixture was poured into a stirred mixture of sodium bicarbonate (800 mg) in 0.5 M sodium thiosulfate solution (11 mL) and dichloromethane (50 mL). The mixture was stirred vigorously until the two layers were clear. The dichloromethane layer was separated, washed with brine, dried over anhydrous magnesium sulfate and evaported in vacuo to give 310 mg (97.6%) of compound 35-E as a thin layer chromatography-homogeneous oil (silica gel, ethyl acetate, $R_f$=0.6) with consistent $^1$H-NMR and $^{13}$C-NMR spectra. This oil was used in the next step without purification.

35-F.
(5RS*,trans)-7-[1-[(4-Fluorophenyl)methyl]-3-(1-methylethyl)-5-oxo-2-pyrrolidinyl]-5-hydroxy-3-oxo-6-heptynoic acid, methylester Sodium hydride (60% dispersion in mineral oil, 65 mg, 1.62 mmol) was washed twice with dry hexane, dried briefly in vacuo, suspended in dry tetrahydrofuran (10 mL), cooled in an ice bath and stirred under an atmosphere of nitrogen. A solution of methyl acetoacetate (175 μl, 1.62 mmol) in dry tetrahydrofuran (3 mL) was added dropwise, followed after 30 minutes by dropwise n-butyl lithium (2.5 M solution in hexane, 650 μl, 1.62 mmol). After another 30 minutes, the solution was cooled to −40° (dry ice-acetonitrile bath) and a solution of compound 35-E (310 mg, 1.08 mmol) in dry tetrahydrofuran (2 mL) was added dropwise. After 3 hours, the resulting solution was quenched with acetic acid (150 mg), warmed to room temperature, diluted with brine (25 mL) and extracted with ethyl acetate (3×25 mL). The combined ethyl acetate extracts were washed with a saturated sodium bicarbonate solution and brine, dried over anhydrous magnesium sulfate and evaporated in vacuo to give an oil. This oil was chromatographed on a column of silica gel (Baker 60-200 mesh, 40 g) eluting successively with ethyl acetate-hexane (4:6) and 1:1) to give 190 mg (43.5%) of thin layer chromatography-homogeneous compound 35-F (silica gel, ethyl acetate, $R_f$=0.45) as an oil with consistent $^1$H-NMR and $^{13}$C-NMR spectra.

35-G.
(5R*,3S*,trans)-7-[1-[(4-Fluorophenyl)-methyl]-3-(1-methylethyl)-5-oxo-2-pyrrolidinyl]-3,5-dihydroxy-6-heptynoic acid, methylester A mixture of compound 35-F (190 mg, 0.471 mmol) triethylborane (1.0 M solution in tetrahydrofuran, 706 μl, 0.706 mmol) and pivalic acid (5 mg) in dry tetrahydrofuran (2.5 mL) was stirred for 30 minutes at room temperature under an atmosphere of nitrogen and then cooled to −78° (dry ice-acetone bath). Sodium borohydride (22.3 mg, 0.589 mmol) was added followed dropwise by dry methanol (1.8 mL). After 2 hours, a solution of 30% hydrogen peroxide (3 mL) in water (2 mL) was added dropwise. The mixture was then warmed up to room temperature, stirred for 1.5 hours and acidified with 5% hydrochloric acid to a pH of 3. After another hour, the organic solvent was evaporated in vacuo. The residual slurry was diluted with brine (20 mL) and extracted with ethyl acetate (4×20 mL). The combined ethyl acetate extracts were washed with brine, dried over anhydrous magnesium sulfate and evaporated in vacuo to give a gum. This gum was chromatographed on a column of silica gel (Baker 60-200 mesh, 30 g) eluting successively with ethyl acetate-dichloromethane (1:4 and 1:1) to give 127 mg (66.5%) of Example 35 as a TLC-homogeneous gum (silica gel, ethyl acetate, $R_f$=0.3) with consistent $^1$H-NMR and $^{13}$C-NMR spectra.

EXAMPLE 36

(3R*,5S*,trans)-7-[1-[(4-Fluorophenyl)methyl]-3-(1-methylethyl)-5-oxo-2-pyrrolidinyl]-3,5-dihydroxy-6-heptynoic acid, monolithium salt A stirred solution of Example 35 (127 mg, 0.313 mmol) in tetrahydrofuran (3 mL) at room temperature under an atmosphere of nitrogen was treated with 1.0 N lithium hydroxide (344 µl, 0.344 mmol). After 1.0 hour, the organic solvent was evaporated in vacuo. The residue was dissolved in water and chromatographed on a column of HP-20 (1"×1" column bed) eluting with deionized, distilled water (250 mL) and 30% methanol-water (250 mL) to give in the later eluate thin layer chromatography-homogeneous Example 36. This later eluate was evaporated in vacuo and lyophilized overnight to give 90 mg (72.3%) of a hydrated analytical specimen of Example 36 as a white solid with consistent IR Mass and $^1$H-NMR spectral data.

Analysis calculated for $C_{21}H_{25}FNO_5Li \cdot 0.33 H_2O$: C, b 62.53; H,6.41; N,3.47; F,4.71. Found: C,62.61; H,6.39; N,3.39; F,4.62.

IR Spectrum (KBr): $\mu_{max}$3424 cm$^{-1}$ (OH), 1671 cm$^{-1}$ (C=O amide), 1587 cm$^{-1}$, 1602 cm$^{-1}$ (C=O acid salt), 1510 cm$^{-1}$ (aromatic c=c).

Mass: (M+ )$^+$=398, (M+Li)$^+$+Li=404, (M-H)$^-$=390, (M-H)$^-$+Li=396.

$^1$H-NMR Spectrum of Example 36 (DMSO-d$_6$, GX400): δ 0.80 and 0.88 (2d, 6H, J=~8.0, H$_{13}$+H$_{14}$), 1.47 (m,1H,H$_{12}$), 1.64 (m,2H,H$_4$), 1.84 (dd,1H,J=~8.0,H$_{10a}$), 2.08 (m,3H,H$_9$+H$_2$), 2.45 (dd,1H,J=~8.0,H$_{10b}$), 3.75 (m,1H,H$_5$), 3.86 (d,1H,J=~8.0 ,H$_8$), 4.05 (dd,1H,J=~1.60,H$_{15a}$), 4.40 (m,1H,H$_3$), 4.76 (d,1H,H$_{15b}$), 5.38 (broad, 1H,OH), 7.16 and 7.28 (2m,4H,H$_{17}$+H$_{18}$+H$_{20}$+H$_{21}$) ppm.

What is claimed is:

1. A compound of the formula

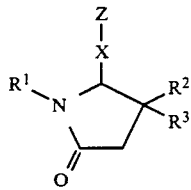

and pharmaceutically acceptable salts thereof, wherein:
Z is

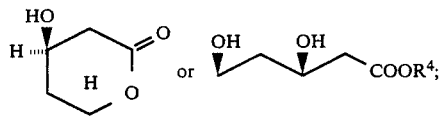

X is lower alkyl, lower alkenyl, or lower alkynyl;
$R^1$ is hydrogen, alkyl, alkenyl, aryl, alkylaryl, or substituted aryl having substituents $R^5$ and $R^6$;
one of $R^2$ and $R^3$ is hydrogen, and the other is hydrogen, alkyl, alkenyl, aryl, substituted aryl having substituents $R^7$ and $R^8$, alkylaryl, and alkyl-substituted aryl having substituents $R^7$ and $R^8$; or $R^2$ and $R^3$ are both lower alkyl; or $R^2$ and $R^3$ together complete a hydrocarbon ring that is
(1) cycloalkyl,
(2) cycloalkenyl,
(3) substituted cycloalkyl having substituents $R^5$ and $R^6$,
(4) substituted cycloalkenyl having substituents $R^5$ and $R^6$;
$R^4$ is selected from:
(1) hydrogen,
(2) ammonium,
(3) mono-, di-, or trialkylammonium,
(4) alkali metal,
(5) alkyl,
(6) alkyl substituted with phenyl,
(7) alkylarylamine, and
(8) diarylalkylamine;
$R^5$ and $R^6$ are each independently selected from:
(1) alkyl,
(2) substituted alkyl having one or more substituents selected from:
(i) halogen,
(ii) nitro,
(iii) hydroxy,
(iv) alkoxy,
(v) alkoxycarbonyl,
(vi) acyl,
(vii) acyloxy,
(viii) cyano,
(ix) aryl,
(x) substituted aryl having substituents $R^7$ and $R^8$,
(xi) alkyl-S(O)$_n$,
(xii) dialkylamino,
(xiii) cycloalkyl-S(O)$_n$,
(xiv) aryl-S(O)$_n$,
(xv) substituted aryl-S(O)$_n$, having substituents $R^7$ and $R^8$, and
(xvi) oxo,
(3) alkyl-S(O)$_n$,
(4) cycloalkyl-S(O)$_n$,
(5) aryl-S(O)$_n$,
(6) substituted aryl-S(O)$_n$ having substituents $R^7$ and $R^8$,
(7) halogen,
(8) hydroxy,
(9) alkoxy,
(10) alkoxycarbonyl,
(11) acyloxy,
(12) aryl,
(13) substituted aryl having one or more substituents $R^7$ and $R^8$,
(14) cycloalkenyl-S(O)$_n$, and
(15) hydrogen;
$R^7$ and $R^8$ are each independently hydrogen, halogen, trifluoromethyl, alkyl, nitro, alkoxy, or cyano; and n is 0, 1, or 2.

2. The compound of claim 1, wherein X is —CH$_2$CH$_2$—.

3. The compound of claim 1, wherein X is —CH=CH—.

4. The compound of claim 1, wherein X is —C≡C—.

5. The compound of claim 1, wherein $R^4$ is lithium.

6. The compound of claim 1 wherein $R^1$ is —CH$_2$-phenyl.

7. The compound of claim 1 wherein $R^1$ is isopropyl.

8. The compound of claim 1 wherein $R^1$ is fluoro-substituted phenyl.

9. The compound of claim 1 wherein one of $R^2$ and $R^3$ is lower alkyl and the other is hydrogen.

10. The compound of claim 1 wherein one of $R^2$ and $R^3$ is phenyl and the other is hydrogen.

11. The compound of claim 1 wherein one of $R^2$ and $R^3$ is fluoro-substituted phenyl and the other is hydrogen.

12. The compound of claim 1 wherein one of $R^2$ and $R^3$ is —$CH_2$— fluoro-substituted phenyl and the other is hydrogen.

13. The compound of claim 1 wherein one of $R^2$ and $R^3$ is isopropyl and the other is hydrogen.

14. The compound of claim 1 wherein $R^2$ and $R^3$ comprise a cyclopentyl ring.

15. The compound of claim 1 wherein one of $R^1$, $R^2$, and $R^3$ is fluoro-substituted phenyl.

16. The compound of claim 1 wherein one of $R^1$, $R^2$ and $R^3$ is —$CH_2$— fluoro-substituted phenyl and the other is hydrogen.

17. The compound of claim 1 wherein one of $R^1$, $R^2$ and $R^3$ is isopropyl.

18. The compound of claim 1 having the name (3R,5S,6E,cis)-3,5-Dihydroxy-7-[3-methyl-5-oxo 1-(phenylmethyl)-2-pyrrolidinyl]-6-heptenoic acid, monolithium salt.

19. The compounds of claim 1 having the names:
(3R,5S,6E,cis)-3,5-Dihydroxy-7-[3-methyl-5-oxo-1-(phenylmethyl)-2-pyrrolidinyl]-6-heptenoic acid, methyl ester;
(3R,5S,6E,cis).3,5-Dihydroxy-7-[3-methyl-5-oxo-1-(phenylmethyl)-2-pyrrolidinyl]-6-heptenoic acid, monolithium salt;
(3R,5S,6E,trans)-3,5-Dihydroxy-7-[3-methyl-5-oxo-1-(phenylmethyl)-2-pyrrolidinyl]-6-heptenoic acid, methylester;
(3R,5S,6E,trans) 3,5-Dihydroxy-7-[3-methyl-5-oxo-1-(phenylmethyl)-2-pyrrolidinyl]-6-heptenoic acid, monolithium salt;
(3R,5S,cis)-3,5-Dihydroxy-7-[3-methyl-5-oxo-1-(phenylmethyl)-2-pyrrolidinyl]heptanoic acid, methylester;
(3R,5S,cis)-3,5-Dihydroxy-7-[3-methyl-5-oxo-1-(phenylmethyl)-2-pyrrolidinyl]heptanoic acid, monolithium salt;
(3R,5S,trans)-3,5-Dihydroxy-7-[3-methyl-5-oxo-1-(phenylmethyl)-2-pyrrolidinyl]heptanoic acid, methylester;
(3R,5S,trans)-3,5-Dihydroxyl-b 7-[3-methyl-5-oxo-1-(phenylmethyl)-2-pyrrolidinyl]heptanoic acid, monolithium salt;
(3R,5S,6E,trans)-7-[3-(4-Fluorophenyl)-1-(1-methylethyl)-5-oxo-2-pyrrolidinyl]-3,5-dihydroxy-6-heptenoic acid, methylester;
(3R,5S,6E,trans)-7-[3-(4-Fluorophenyl)-1-(1-methylethyl)-5-oxo-2-pyrrolidinyl]-3,5-dihydroxy-6-heptenoic acid, monolithium salt;
(3R,5S,trans)-7-[3-(4-Fluorophenyl)-1-(1-methylethyl)-5-oxo-2-pyrrolidinyl]-3,5-dihydroxy-heptanoic acid, methylester;
(3R,5S,trans)-3-(4-Fluorophenyl)-3,5-dihydroxy-1-(1-methylethyl)-5-oxo-2-pyrrolidine-heptanoic acid, monolithium salt;
(3R,5S,6E,cis)-7-[3-(4-Fluorophenyl)-1-(1-methylethyl)-5-oxo-2-pyrrolidinyl]-3,5-dihydroxy-6-heptenoic acid, methylester;
(3R,5S,6E,cis)-7-[3-(4-Fluorophenyl)-1-(1-methylethyl)-5-oxo-2-pyrrolidinyl]3,5-dihydroxy-6-heptenoic acid, monolithium salt;
(3R,5S,cis)-7-[3-(4-Fluorophenyl)-1-(1-methylethyl)-5-oxo-2-pyrrolidinyl]3,5-dihydroxy-heptanoic acid, methylester;
(3R,5S,cis)-3-(4-Fluorophenyl)-3,5-dihydroxy-1-(1-methylethyl)-5-oxo-2-pyrrolidine-heptanoic acid, monolithium salt;
(3R,5S,6E,cis)-7-[1- [(4-Fluorophenyl)methyl]-3-(1 methylethyl)-5-oxo-2-pyrrolidinyl]-3,5-dihydroxy-6-heptenoic acid, methylester;
(3R,5S,6E,cis)-7-[1-[(4-Fluorophenyl)methyl]-3-(1-methylethyl)-5-oxo-2-pyrrolidinyl]-3,5-dihydroxy 6-heptenoic acid, monolithium salt;
(3R,5S,6E,trans)-7-[1-[(4-Fluorophenyl)methyl]-3-(1-methylethyl)-5-oxo-[2-pyrrolidinyl]-3,5-dihydroxy-6-heptenoic acid, methylester;
(3R,5S,6E,trans)-7-[1-[(4-Fluorophenyl)methyl]-3-(1-methylethyl)-5-oxo-2-pyrrolidinyl]-3,5-dihydroxy-6-heptenoic acid, monolithium salt;
(3R,5R,trans)-7-[1-[(4-Fluorophenyl)methyl]-3-(1-methylethyl)-5-oxo-[2-pyrrolidinyl]-3,5-dihydroxy-6-heptanoic acid, methylester;
(3R,5S,trans) 1-[(4-Fluorophenyl)methyl]-3,5-dihydroxy-3-(1-methylethyl)-5-oxo-2-pyrrolidine-heptanoic acid, monolithium salt;
(3R,5R,cis)-3,5-Dihydroxy-1-[(4-fluorophenyl)methyl]-3-(1-methylethyl)-5-oxo-2-pyrrolidine-heptanoic acid, methylester;
(3R,5R,cis)-3,5-Dihydroxy-1-[(4-fluorophenyl)methyl]-3-(1-methylethyl)-5-oxo-2-pyrrolidine-heptanoic acid, monolithium salt;
(3R*,5S*,cis)-7-[1-[(4-Fluorophenyl)methyl]-3-(1-methylethyl)-5-oxo-pyrrolidinyl]-3,5-dihydroxy-6-heptynoic acid, methylester;
(3R*,5S*,cis)-7-[1-[(4-Fluorophenyl)methyl]-3-(1-methylethyl)-5-oxo2-pyrrolidinyl]-3,5-dihydroxy-6-heptynoic acid, monolithium salt;
(R*,S*)-7-[2-(4-Fluorophenyl)-3-oxo-2-azaspiro[4,4]non-1-yl]-3,5-dihydroxy-6-heptenoic acid, monolithium salt;
(R*,S*)-7- [2-(4-Fluorophenyl)-3-oxo-2-azaspiro-[4,4]nonyl]-3,5-dihydroxy 6-heptenoic acid, monolithium salt;
(R*,S*)-7-[2-(4-Fluorophenyl)-3-oxo-2-azaspiro-[4,4]-non-1-yl]-3,5-dihydroxy heptanoic acid, methylester;
(R*,S*)-7- [2-(4-Fluorophenyl)-3-oxo-2-azaspiro[4,4-]non1-yl]-3,5-dihydroxy-heptanoic acid, monolithium salt;
(3R*,5S*,6E,trans)-7-[1-(4-Fluorophenyl)-3-(1-methylethyl)-5-oxo-2-pyrrolidinyl]-3,5-dihydroxy-6-heptenoic acid, monolithium salt;
(3R*,5S*,6E,trans) -7-[1-(4-Fluorophenyl)-3-(1-methylethyl)-5-oxo-2-pyrrolidinyl]-3,5-dihydroxy-6-heptenoic acid, monolithium salt;
(3R,5S,trans)-1-(4-Fluorophenyl)-3,5-dihydroxy.3-(1-methylethyl)-5-oxo-2-pyrrolidine-heptanoic acid, methylester;
(3R,5S,trans)-1-(4-Fluorophenyl)-3,5-dihydroxy-3-(1-methylethyl)-5-oxo-2-pyrrolidine-heptanoic acid, monolithium salt;
(5R*,3S*,trans)-7-[1-[(4-Fluorophenyl)methyl]-3-(1-methylethyl)-5-oxo-2-pyrrolidinyl]-3,5-dihydroxy-6-heptynoic acid, methylester; and
(3R*,5S*,trans)-7-[1-[(4-Fluorophenyl)methyl]-3-(1-methylethyl)-5-oxo-2-pyrrolidinyl]-3,5-dihydroxy-6-heptynoic acid, monolithium salt.

20. A compound of the formula

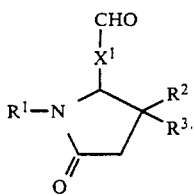

wherein:
X¹ is a bond or alkynyl;
R¹ is hydrogen, alkyl, alkenyl, aryl, alkylaryl, or substituted aryl having substituents R⁵ and R⁶;
one of R² and R³ is hydrogen and the other is hydrogen, alkyl, alkenyl, aryl, substituted aryl having substituents R⁷ and R⁸, alkyl aryl, or alkyl-substituted aryl having substituents R⁷ and R⁸; or R² and R³ are both lower alkyl; or R² and R³ together complete a hydrocarbon ring that is
(1) cycloalkyl,
(2) cycloalkenyl,
(3) substituted cycloalkyl having substituents R⁵ and R⁶,
(4) substituted cycloalkenyl having substituents R⁵ and R⁶;
R⁴ is selected from:
(1) hydrogen,
(2) ammonium,
(3) mono-, di-, or trialkylammonium,
(4) alkali metal,
(5) alkyl,
(6) alkyl substituted with phenyl,
(7) alkylarylamine, and
(8) diarylalkylamine;
R⁵ and R⁶ are each independently selected from:
(1) alkyl,
(2) substituted alkyl having one or more substituents selected from:
  (i) halogen,
  (ii) nitro,
  (iii) hydroxy,
  (iv) alkoxy,
  (v) alkoxycarbonyl,
  (vi) acyl,
  (vii) acyloxy,
  (ix) aryl,
  (x) substituted aryl having substituents R⁷ and R⁸,
  (xi) alkyl-S(O)$_n$,
  (xii) dialkylamino,
  (xiii) cycloalkyl-S(O)$_n$,
  (xiv) aryl-S(O)$_n$,
  (xv) substituted aryl-S(O)$_n$ having substituents R⁷ and R⁸, and
  (xvi) oxo,
(3) alkyl-S(O)$_n$,
(4) cycloalkyl-S(O)$_n$,
(5) aryl-S(O)$_n$,
(6) substituted aryl-S(O)$_n$ having substituents R⁷ and R⁸,
(7) halogen,
(8) hydroxy,
(9) alkoxy,
(10) alkoxycarbonyl,
(11) acyloxy,
(12) aryl,
(13) substituted aryl having substituents R⁷ and R⁸,
(14) cycloalkenyl-S(O)$_n$, and
(15) hydrogen;
R⁷ and R⁸ are each independently hydrogen, halogen, trifluoromethyl, alkyl, nitro, alkoxy, or cyano; and
n is 0, 1, or 2.

21. A method of inhibiting HMG-CoA reductase in a mammal, which comprises administering an effective amount of the compound of claim 1.

22. A method of reducing cholesterol levels in a mammal, which comprises administering an effective amount of the compound of claim 1.

23. A method of treating atherosclerosis, which comprises administering an effective dose of a compound as described in claim 1.

24. A method of treating hyperlipidemia, which comprises administering an effective dose of a compound as described in claim 1.

25. A method of increasing plasma high-density lipoprotein cholesterol levels, which comprises administering an effective dose of a compound as described in claim 1.

26. A pharmaceutical composition having antihypercholesterolemic activity, which comprises an effective amount of a compound of claim 1 and in inert carrier therefor.

* * * * *